(12) United States Patent
Regnier et al.

(10) Patent No.: US 8,455,202 B2
(45) Date of Patent: Jun. 4, 2013

(54) AFFINITY SELECTOR BASED RECOGNITION AND QUANTIFICATION SYSTEM AND METHOD FOR MULTIPLE ANALYTES IN A SINGLE ANALYSIS

(75) Inventors: Fred E. Regnier, West Lafayette, IN (US); Nicholas B. Herold, Lafayette, IN (US); Kevin W. Meyer, West Lafayette, IN (US)

(73) Assignee: Perfinity Biosciences, Inc., West Lafayette, IN (US)

( * ) Notice: Subject to any disclaimer, the term of this patent is extended or adjusted under 35 U.S.C. 154(b) by 112 days.

(21) Appl. No.: 12/721,173

(22) Filed: Mar. 10, 2010

(65) Prior Publication Data
US 2011/0223683 A1    Sep. 15, 2011

(51) Int. Cl.
*G01N 33/53*    (2006.01)

(52) U.S. Cl.
CPC .................... *G01N 33/53* (2013.01)
USPC ........... 435/7.1; 435/7.92; 436/501; 436/518; 436/538

(58) Field of Classification Search
None
See application file for complete search history.

(56) References Cited

U.S. PATENT DOCUMENTS

| | | | |
|---|---|---|---|
| 5,696,375 A * | 12/1997 | Park et al. | 250/287 |
| 2002/0150926 A1 | 10/2002 | Jindal et al. | |
| 2007/0142629 A1 | 6/2007 | Guerrier et al. | |
| 2008/0145863 A1 | 6/2008 | Regnier | |

OTHER PUBLICATIONS

Gygi et al., Quantitative analysis of complex protein mixtures using isotope-coded affinity tags, Nature Biotechnology, vol. 17, Oct. 1999, pp. 994-999.*

Written Opinion and International Search Report for PCT/US10/26819 (7 pages), Sep. 26, 2011.
Y. L. Frank Hsieh, Hongqi Wang, Chris Elicone, Jonathan Mark, Stephen A. Martin, and Fred Regnier, Automated Analytical System for the Examination of Protein Primary Structure, Anal. Chem., 1996, 68 (3), pp. 455-462.
Janis LJ, Regnier FE., Dual-Column Immunoassays Using Protein G Affinity Chromatography. Anal Chem. Sep. 1, 1989;61(17):1901-6.
Nelson, R. W., Dogruel, D., Krone, J. R., and Williams, P., Peptide Characterization Using Bioreactive Mass Spectrometer Probe Tips, Rapid Commun. Mass Spectrom., 9, 1380-1385 (1995).
Nelson, R. W., Krone, J. R., Bieber, A. L., and Williams, P., Mass Spectrometric Immunoassay, Anal. Chem., 67, 1153-1158 (1995).
Chapman, K. The Proteinchip® Biomarker System from Ciphergen Biosystems: a novel proteomics platform for rapid biomarker discovery and validation. Biochemical Society Transactions 30, 2 (2002).
Anderson, N.L., Anderson, N.G., Haines, L.R., Hardie, D.B., Olafson. R.W., and Pearson, Mass Spectrometric Quantitation of Peptides and Proteins Using Stable Isotope Standards and Capture by Anti-Peptide Antibodies (SISCAPA). T.W. Journal of Proteome Research 3: 235-44 (2004).

* cited by examiner

*Primary Examiner* — Gary W Counts
(74) *Attorney, Agent, or Firm* — Faegre Baker Daniels LLP

(57) ABSTRACT

A multi-dimensional method for simultaneously analyzing multiple analytes within a sample solution, comprising adding affinity selectors to a sample solution containing analytes to be measured, the affinity selectors having an affinity for one or more of the analytes within the sample solution; allowing immune complexes to form between the affinity selectors and the analytes; partially or totally resolving the formed immune complexes from non-analyte substances within the sample solution; dissociating the resolved immune complexes; separating the analytes and the affinity selectors of the dissociated immune complexes from one another by capturing the analytes through a surface adsorption process; transferring the captured analytes to a detection means; and resolving the analytes with the detection means in accordance with their mass-to-charge ratios.

12 Claims, 13 Drawing Sheets

AFFINITY SELECTOR BASED RECOGNITION AND QUANTIFICATION SYSTEM AND METHOD FOR MULTIPLE ANALYTES IN A SINGLE ANALYSIS

TECHNICAL FIELD OF THE DISCLOSURE

The present invention relates generally to a multi-dimensional analytical strategy and system for analyzing antigens and particularly to an affinity selector based recognition and quantification system and method for analyzing multiple analytes in a single analysis.

BACKGROUND OF THE DISCLOSURE

Determining a single analyte in a mixture of ~100,000 other components is a formidable task. More than 60 years ago, analysts began to recognize that the structural selectivity of antibodies could be used to bind and purify antigens and haptens from biological extracts or blood on the basis of their chemical structure. This technique became so important that Rosalyn Yalow was awarded the Nobel Prize for radio-immunological assays (RIA) in 1960. Along with enzyme linked immunosorbent assays (ELISA), these two technologies provided the world with a simple method to measure antigens down to the pg/mL level.

A fundamental component of both RIA and ELISA is the use of immobilized antibodies to achieve antigen selection from samples in the first step of an assay. Since the inception of these approaches, analytical immunologists have understood that binding antibodies at a surface introduces significant kinetic limitations. For instance, antigens have to travel substantial distances in terms of molecular dimensions to reach surfaces, thereby adding to the amount of time needed for antigen binding to occur in a test tube or microtiter well. Moreover, all antibodies used in an assay are bunched together at the surface of an assay well or on a particle, while antigens are uniformly distributed throughout the solution. When an ELISA is carried out in a microtiter well, incubation times of a day or more are typically used to allow time for the antigens to diffuse to the walls of the well where the antibodies are bound. Efforts to minimize the diffusion problems in the case of RIA involved using large numbers of very small inorganic particles to which antibodies were immobilized. Over the course of the past several years, many types of mixing, flow, heating, and even sonication procedures have been used to minimize the diffusion problem noted above. Despite these efforts, diffusion problems still exist.

As analytical chemistry has evolved, it has been recognized that better and more complete answers can be obtained to various questions involving a sample if multiple analytes are determined simultaneously. This in turn has led to an increased interest in "analytical multiplexing", where large numbers of analytes are analyzed in a sample during the course of a single analysis. This is often done through immunological arrays.

Interest in immunological arrays stems from the popularity and success of micro-electro-mechanical-systems (MEMS). While several types of antibody arrays have been used for large scale multiplexing, including high throughput and parallel processing techniques, other approaches have focused on large scale multiplexing with smaller numbers of samples, such as would be needed in a clinical laboratory that is concerned about minimizing the total analysis time and cost per assay. No matter what approach is utilized, immunological array systems still face challenges with respect to antibody immobilization and kinetics. There are also issues with respect to whether antibodies will retain full activity after immobilization, particularly if they are improperly oriented at the surface. Steric issues must also be considered, particularly in terms of the orientation of the antibody to the surface, as well as its packing density. Finally, reproducibility is also a factor, particularly as it is very difficult to reproduce immobilized antibodies from picoliter volumes of solution deposited on a surface. Evaporation, as well as a myriad of other phenomena, also diminishes reproducibility from that experienced at the titer plate level of immobilization.

Although the distance antigens must diffuse to reach surfaces is smaller in an immunological array than in a microtiter well, kinetic issues are still a serious limitation with immunological arrays. This is particularly true at low antigen concentrations. A substantial amount of time is required for an antigen to diffuse from all points in the solution to one of the array elements. Because molecular docking in antigen:antibody complex formations requires precise spatial orientation, antigens generally strike surfaces many times before establishing the correct capturing orientation. For instance, if an antigen is not captured after colliding with the surface on a 128 element array, it has a lot of space to navigate before striking the surface a second time.

As noted above, particle based assays began with the RIA and Yalow approaches. Currently the Yalow approach has evolved into two types of assay systems: 1) a particle approach used in flow cytometry assays (e.g., the Luminex system) where the fluorescence of individual particles is examined; and 2) an approach where antibodies are placed on a magnetic particle where the immune complex is formed, and the particle is then pulled out of solution and the antigens released for further measurements (e.g., the SISCAPA system of Leigh Anderson). Multiplexing requires the preparation of a different set of immunosorbent beads for each antigen being determined. This means that 20-50 different sets of antibody carrying beads would need to be added to the sample solution, thereby causing even larger kinetic limitations of the antigens in terms of finding the appropriate antibody particle. In addition, the solution becomes crowded with so many particles that the antigens must diffuse around particles not carrying their antibody. One proposed solution for dealing with these limitations is to immobilize multiple antibodies on a single particle. However, this solution does not completely address the issues of diffusion and stoichiometric control. Moreover, the dilution of antibody concentration on the particle surface means that the antigens can strike particle surfaces, while not contacting their antibody. In addition, the total surface area, and thus the total number of particles required, would still remain high.

With respect to the flow cytometry strategy (such as the Luminex system), immune complexes must be formed on the particle surfaces before they can be analyzed by flow cytometry. While this system is very similar to the above, each bead carries a single antibody targeting a single antigen. Again, there is the diffusion problem in antigen capture.

It is interesting that the function of mammalian immune systems is to deal with thousands of antigens, albeit not all of them simultaneously. As immunity to foreign substances develops in an individual mammal, antibodies to thousands of immunogens are produced. These antibodies are contained within the immunoglobulins circulating in blood where at any time, hundreds of antigens are being sequestered as antigen:antibody complexes are formed. Upon analyzing mammalian immune systems, it can be concluded that antibodies have evolved to function in solution as they form immune complexes. In addition to functioning in solution, they also sequester large numbers of antigens at the same time and have few of the limitations seen within immobilized antibody assay systems.

The above-noted observations of mammalian immune systems are extremely important, particularly as they clearly suggest that the formation of immune complexes in solution are naturally efficient, while the formation of complexes on immobilized surfaces are not. Moreover, it is clear that several immune complexes can be simultaneously formed in a solution (such as blood), which is a necessary factor to achieve when performing an analytical multiplexing process. Finally, most of the problems that commonly impact immunological assays (e.g., loss of activity during immobilization, proper orientation of antibodies, diffusion kinetics and having sufficient surface area) are not prevalent within these natural solution based systems.

Despite the above-described advantages of naturally formed immune complexes, such immunological assays still require the addition of antibodies to the samples, which can be concerning. For instance, adding large numbers of antibodies to a plasma sample may cause the protein concentration to increase to such a level that analyte diffusion is hampered. While this issue may seem concerning on its face, upon taking a further look, it can be concluded that this issue is likely inconsequential. More particularly, the average concentration of serum albumin in plasma is present in the range of about 50 to about 100 mg/mL, while immunoglobulins are present in an amount of approximately 4 mg/mL, and that of any particular antibody is probably in the range of from about 1 to about 100 ug/mL. If it is assumed that the concentration of an antibody needed to carry out an analytical measurement is 10 ug/mL and when 100 antibodies are to be added to a plasma sample, the total increase in protein concentration would be about 1 mg/mL. Similarly, if the concentration of protein in the plasma sample were 75 mg/mL, the increase in protein concentration would be about 1.3%. As such, it can be concluded that the addition of 100 antibodies to plasma to carry out a 100-fold multiplexed analysis would have almost no effect on protein concentration, solution viscosity, and ultimately analyte diffusion. Moreover, adding a thousand antibodies would only add 10 mg/mL of mass, or a 14% change in protein concentration; which again, would likely not be enough to impact the analysis.

Prior to 1960, immunological assays generally targeted individual antigens and were carried out in solution through a process called the 'precipitin reaction'. Subsequent to immune complex formation, the polyclonal antibody mixture being used in the assay either formed a precipitate, or was induced to do so by the addition of a carbohydrate or an ethylene glycol polymer. Antigen concentration was determined by light scattering; however, the lack of sensitivity and linearity associated with this approach, as well as the fact that the precipitin assay only permitted one antigen to be assayed at a time, led to the demise of the method, and ultimately a transition to the far more sensitive RIA and ELISA methods. Despite the failures of the precipitin reaction method, it can still be reasoned that solution based immune complex formation approaches could be useful for immunological assays if selectivity and detection sensitivity were vastly improved.

Although the original precipitin and RIA approaches depended on a single method of selection (i.e. one antibody) in the execution of antigen measurements, it is accepted today that a sole antibody is not sufficiently selective to discriminate between an antigen and all the other chemical entities in a sample. Current immunological assays are built on multiple dimensions of selection and/or discrimination, and it is particularly ideal if each of these dimensions is of orthogonal selectivity.

SUMMARY OF THE INVENTION

The present invention overcomes or ameliorates at least one of the prior art disadvantages discussed above or provides a useful alternative thereto by providing a novel multi-dimensional analytical strategy and system for analyzing antigens.

In one form thereof, a multi-dimensional analytical strategy for antigen analysis is provided. In accordance with this aspect of the present invention, antigens in a sample solution are sequestered by antibodies in a soluble immune complex during the first dimension of analysis. The antibodies being added to the solution at the beginning of the analytical process are for the specific purpose of binding antigens for qualitative and quantitative analyses in subsequent steps of the multi-dimensional process. Cross-reacting antigens, non-specifically bound substances, and species that associate secondarily with antigens, may also adsorb to immune complexes in the first dimension and are eliminated in later dimensions of analysis. Unique features of the immune complexes formed in the first dimension are then exploited in the second dimension of analysis to resolve them from other components in samples on the basis of their hydrodynamic volume using a molecular sizing system or sorbent media that target a specific feature of the sequestering antibody. Fractionation based on either of these two features is orthogonal to epitope:paratope recognition, and discrimination in the third and fourth dimensions is achieved in a combination of ways ranging from analyte specific chemical modifications (such as derivatization or proteolysis) and size discrimination along with adsorption and differential elution from surfaces (such as those on reversed phase or ion exchange media) or a combination of sizing exclusion and hydrophobic adsorption (as with restricted access media). The particular discrimination mechanism chosen, and the order in which they are coupled, depends on the chemical nature of the analytes being targeted and the fractionation mechanisms used in the first two dimensions. Dimensions of analysis in the fifth dimension and beyond occur within detection systems ranging from mass spectrometry to fluorescence and electrochemical detectors. In accordance with certain embodiments utilizing a mass spectrometry detection system, the analytes can be resolved according to their mass in the fifth dimension, collision induced dissociation of analytes in a sixth dimension, and mass analysis of the resulting fragment ions in a seventh dimension.

In accordance with another form of the present invention, a multi-dimensional method for simultaneously analyzing multiple analytes within a sample solution is provided. According to this aspect of the invention, the method comprises adding affinity selectors to the sample solution to form immune complexes between the affinity selectors and the analytes; providing a first separation means to partially or totally resolve the formed immune complexes from other non-analyte substances within the sample solution; providing a second separation means to partially or totally resolve the analytes from one another within the sample solution; and resolving the analytes according to their mass-to-charge ratio.

In accordance with still other aspects of the present invention, a multi-dimensional method for simultaneously analyzing multiple analytes within a sample solution is provided. In accordance with this aspect of the invention, the method comprises adding affinity selectors to a sample solution containing analytes to be measured, the affinity selectors having an affinity for one or more of the analytes within the sample solution; allowing immune complexes to form between the affinity selectors and the analytes; partially or totally resolving the formed immune complexes from non-analyte substances within the sample solution; dissociating the resolved immune complexes; separating the analytes and the affinity selectors of the dissociated immune complexes from one another by capturing the analytes through a surface adsorption process; transferring the captured analytes to a detection means; and resolving the analytes with the detection means in accordance with their mass-to-charge ratios.

In certain aspects of the present invention, the formed immune complexes are totally or partially resolved by separating the analytes or formed immune complexes according to their hydrodynamic volume, targeting a unique structural feature of the affinity selectors or the analytes to capture antibodies of the analytes or formed immune complexes, hybridizing oligonucleotides or adsorbing and capturing biotinylated affinity selectors with immobilized avidin.

In yet other aspects of the present invention, the analytes and affinity selectors within the sample solutions are separated from one another by separating the analytes or formed immune complexes according to their hydrodynamic volume, adsorbing and differentially eluting the analytes from a hydrophobic surface, targeting a unique structural feature of the affinity selectors or the analytes to capture antibodies of the analytes or formed immune complexes, hybridizing oligonucleotides, capturing biotinylated affinity selectors with immobilized avidin, adsorbing and differentially eluting the analytes from a charged surface, adsorbing and differentially eluting the analytes from an immobilized metal affinity chelator, or adsorbing and differentially eluting the analytes from a boronic acid rich surface.

The analytes under analysis in accordance with the present teachings may include, but are not limited to, at least one of analyte fragments, analyte derivatives and analyte isotopomers. Moreover, the affinity selectors of the present teachings may include, but are not limited to, at least one of an antibody, an antibody fragment, an aptamer, a lectin, a phage display protein receptor, a bacterial protein and an oligonucleotide. In accordance with certain embodiments, the bacterial proteins can include at least one of G proteins, A proteins and proteins that are produced by an organism targeting a protein from another organism, while the oligonucleotide can include at least one of RNA, DNA and PNA.

In accordance with certain embodiments of the present invention, the analytes and the affinity selectors are separated from one another by targeting a unique structural feature of the affinity selectors with an immobilized antibody. In accordance with these specific embodiments, the unique structural feature being targeted may include, but is not limited to, at least one of a distinctive natural structural feature of the affinity selectors, a hapten that has been conjugated to the affinity selectors and an immunogen conjugated to the affinity selectors.

In accordance with some aspects of the present invention, the analytes under analysis include ionized analytes that are detectable using a mass spectrometry analysis that specifically detects parent ions of the analytes that have been separated in accordance to their mass-to-charge ratio.

In certain aspects of the present invention, the analytes are resolved by using a detection means that is configured to perform the integrated steps of: (a) ionizing analytes that have been separated according to their mass-to-charge ratio; (b) generating fragment ions of parent ions from step (a) by utilizing a gas phase fragmentation process; (c) separating the generated fragment ions from step (b) according to their mass-to-charge ratio; and (d) recording a produced relative ion current as the generated fragment ions from step (c) collide with a detector surface. In terms of the detection means that is used to resolve the analytes, in accordance with certain embodiments, the analytes are detected by one or more of the following techniques: mass spectrometry, absorbance, fluorescence and electrochemical analysis.

In accordance with further embodiments of the present invention, isotopically coded internal standards can be used to achieve relative or absolute quantification of the analytes under analysis. Moreover, sequential addition, competitive binding assays can also be used to achieve the relative or absolute quantification of the analytes.

In still other aspects of the present invention, antibody concentration can also be considered to collect an aliquot of an analyte from the sample solution. In accordance with these aspects of the present invention, the collected aliquot is configured to fit an optimum detection range of a device that is being used to resolve the analytes.

In accordance with yet another form of the present invention, a method for analyzing multiple analytes within a sample solution using a plurality of orthogonal separation dimensions is provided. According to this aspect of the invention, the method comprises adding affinity selectors to the sample solution to form immune complexes between the affinity selectors and the analytes and to independently sequester one or more antigens and interfering substances within the sample solution; using a selective adsorption technique to remove in a first or second orthogonal separation dimension, irrespective of order, the sequestered one or more antigens and interfering substances; providing a first separation means to partially or totally resolve the formed immune complexes from other non-analyte substances within the sample solution; providing a second separation means to partially or totally resolve the analytes from one another within the sample solution; and resolving the analytes according to their mass-to-charge ratio.

In accordance with still another aspect of the present invention, a method for simultaneously analyzing analytes within a sample solution is provided, the method comprising adding affinity selectors to the sample solution to form immune complexes between the affinity selectors and the analytes; separating the formed complexes from other non-complexed substances within the sample solution by providing a first chromatographic column; dissociating the formed complexes; separating the analytes from the affinity selectors by capturing the analytes through surface adsorption of a second chromatographic column; transferring the captured analytes to a third chromatographic column that is coupled to the second chromatographic column; and analyzing the captured antigens or fragments thereof as they elute from the third chromatographic column.

In accordance with certain aspects of the present invention, the non-complexed substances comprise substances that do not have an epitope targeted by the added affinity selectors.

In yet other aspects of the present invention, the chromatographic column used to separate the formed complexes from other non-complexed substances within the sample solution is selected from at least one of a size exclusion chromatography column, a restricted access media column packed with a sorbent, an antibody column that is configured to target a general class of the added affinity selectors, a protein A or G column that is configured to target all of the added affinity selectors, a DNA oligonucleotide column having immobilized DNA that is complementary to an oligonucleotide attached to one or more of the added affinity selectors, an avidin column that is configured to target biotin attached to one or more of the added affinity selectors and a chromatography column that is configured to select a naturally occurring or synthetically created feature of the added affinity selectors.

In accordance with still other aspects of the present invention, the chromatographic column used to separate the analytes from the affinity selectors by capturing the analytes through surface adsorption is selected from at least one of a reversed phase chromatography column, a restricted access media column, an immunosorbent, an immobilized metal-ion affinity chromatography column, an ion exchange column and a chromatographic retention mechanism.

In accordance with certain aspects of the present invention, the affinity selectors include, but are not limited to, aptamers, protein A, protein G, phage display proteins, natural receptors, lectins, DNA, RNA, synthetic affinity reagents, or some other species that shows an affinity for the analyte to form a plurality of intermolecular complexes between the affinity capture agents and the analyte.

BRIEF DESCRIPTION OF THE DRAWINGS

The above-mentioned and other advantages of the present invention, and the manner of obtaining them, will become more apparent and the invention itself will be better understood by reference to the following description of the embodiments of the invention taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

As mentioned above, the present invention is generally related to a multi-dimensional analytical strategy and system for analyzing antigens. As will be explained in more detail below, one discriminating feature of the present teachings is the ability to form large numbers of inter-molecular complexes with analytes in sample solutions in a first dimension, followed by some type of inter-molecular complex separation in a second dimension that will generate fractions for further fractionation or chemical reaction in a third dimension followed by very specific types of separation or chemical reactions in a third dimension. In certain aspects of the present teachings, higher dimensions of analysis can then be utilized after the third dimension, and particularly such that at the end of the multidimensional analytical process, it will be the case that either 1) each substance (analyte) being examined can be individually identified and quantified, or 2) a closely related family of analytes can be determined together.

Figure 1:
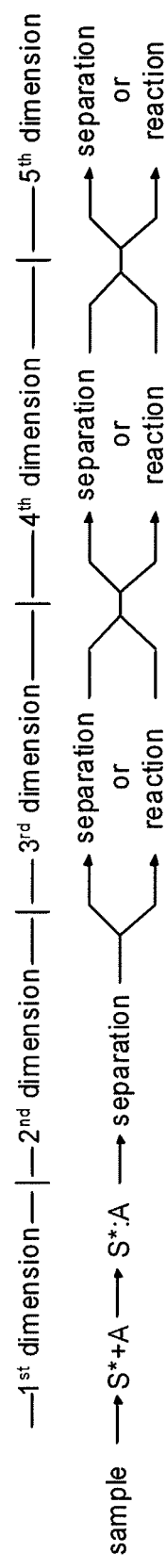
FIG. 1 is a multi-dimensional scheme showing the simultaneous analysis of multiple analytes based on an affinity selector complexing with an analyte to form a complex in accordance with the teachings of the present invention.

Moving now to FIG. 1, a scheme for simultaneous analysis of multiple analytes based on an affinity selector (S*) (such as an antibody, aptamer, lectin, protein G, protein A, phage display protein, or binding protein) complexing with an analyte (A) in the first dimension of analysis to form a complex (S*:A) in accordance with the present invention is shown. While a specific affinity selector will generally be used for each analyte in accordance with certain aspects of the present invention, in other aspects, there can also be affinity selectors that form a complex with multiple analytes, such as would be seen with an antibody targeting the Lewis x antigen that is coupled to many glycoproteins.

With respect to the first dimension (or the "affinity selection dimension"), processes in this dimension are based on complexation of the affinity selector (S*) with an analyte. The symbol (*) on S indicates a unique structural feature of the affinity selector, or complex that may be exploited in selecting it later in a higher dimension.

Analyte analysis in this first dimension starts with the formation of individual complexes in solution as described in formula 1 below:

$$S^* + A_1 \rightleftharpoons S^*{:}A_1 \qquad \text{Formula 1}$$

where S* is an affinity selector such as an IgG or IgM antibody, a lectin, a binding protein, a DNA specie, an RNA specie, or any type of specie with a binding affinity for an analyte (A); S*:A is the non-covalent complex formed by the association of the affinity selector (S*) and a specific analyte (A). A specific affinity selector S* can form a complex with a single analyte or with multiple analytes depending on the selectivity of the affinity selector. An analyte can be an antigen, hapten, or any analyte being measured that has an affinity for S*. An S*:A complex will be formed for each analyte. Placing S* or A in brackets indicates their concentration in moles per liter.

It will generally be the case that:

$$K_{b_1} = \frac{[S^*:A_1]}{[S^*][A_1]} \quad (1)$$

where $K_{b_1}$ is the binding constant of a specific affinity selector for a specific analyte ($A_1$). The binding constant is equal to the rate of complex formation divided by the rate of dissociation. Each type of complex formed in solution will have such a binding constant and can be represented by the general equation:

$$K_{b_n} = \frac{[S^*:A_n]}{[S^*][A_n]} \quad (2)$$

where $A_n$ is any specific analyte.

While not required herein, in certain embodiments, it is beneficial to have an affinity selector with high affinity for the analyte and a large binding constant (e.g., greater than about $10^6$). Moreover, in certain embodiments it is beneficial when the off-rate is low such that the complex S*:A will not dissociate during the subsequent dimensions of analysis unless it is the intent during a specific dimension to dissociate the complex by changing the incubation conditions. In addition, having the complex stay intact during separation from other, non-antigen components in the sample is an important factor to be considered. It should also be noted that while complexes with low binding affinities can be analyzed in the second dimension, it is helpful if the separation is achieved quickly and before the complex has time to dissociate.

In accordance with certain aspects of the present invention, it is desirable that complexes formed between an affinity selector (S*), such as an antibody and an analyte (A), not precipitate. To discourage such precipitation, affinity reagents that do not promote high levels of cross-linking, or perhaps any cross-linking at all, can be used in accordance with these embodiments. When the analytes are of low molecular weight, this will generally not be a problem, particularly as it has been determined that the valence of the affinity selector typically becomes an issue with higher molecular weight analytes. In the case of antibodies, it will be possible to use either polyclonal or monoclonal antibodies when targeting low molecular weight analytes because they are much less likely to form cross-linked precipitates. With proteins and other macromolecular analytes, monoclonal antibodies are less likely to form precipitates. The fact that Fab fragments of antibodies are monovalent makes them a good candidate for an affinity selector agent in accordance with the teachings of the present invention. Moreover, ionic strength, pH, and additives will also play a role in keeping complexes in solution.

In accordance with yet another aspect of the present invention, a sample undergoing analysis is fractionated before immune complex formation or before affinity capture of the immune complex on a solid phase sorbent. The function of the optional step is to remove cross-reacting species, differentiated between natural complexes of which the antigen is a component, differentiate between isoforms of the antigen, or recognize fragments of an antigen. Removal or cross-reacting species before affinity capture of the S*:A complex (shown in Formula 1) greatly facilitates analyte analysis and can be achieved in two ways. First, when the cross-reacting species have some distinguishing feature (e.g., a unique epitope, charge property, or hydrophobicity), they can be selected from the sample either before S*:A complex formation or after S*:A complex formation, but before capture of the complex on an affinity sorbent. Precluding formation of a complex between S* and the cross-reacting (CR) species would be one case while in another the S*:CR complex is removed before S*:A complex is captured.

In yet other embodiments, the antigen is in several different complexes such as S*:A:$P_1$, S*:A:$P_2$, S*:A:$P_3$, and S*:A:$P_4$, and P is one more non-analyte protein, as is common in the interactome or when an antigen is partially or totally complexed with an auto-antibody. This is sometime the case with thyroglobulin in plasma. Moreover, one of these forms may interfere with analysis of the form of antigen associated with a disease. Differentiation between these complexes is achieved by targeting non-analytes in the complex with an immunosorbent that removes one or more forms of the complex before S*:A complex formation or before the S*:A complex is captured. Removal of interfering complexes is achieved with either an immunosorbent targeting the non-analyte in the complex or some other type of adsorbent such as an ion exchanger, an immobilized metal affinity chromatography sorbent, a hydrophobic interaction column, or a size exclusion chromatography column than differentiates between the interfering non-analyte and analyte. Still another use of this step is to differentiate between the native form of antigen and fragments that are of lower molecular weight. It can be the case that either a fragment or the native form of the antigen is the desired analyte being targeted for detection. Again, it should be understood herein that differentiation can be achieved either with an immunosorbent or a size exclusion column, and antigens can exist in post-translationally modified isoforms. As such, this optional step may be used to remove interfering isoforms.

Moving now to FIG. 1 and following complex formation, all S*:A complexes are separated from non-analytes in the second dimension of analysis. This separation step can be carried out in a number of ways, ranging from a highly specific selection process targeting the tag (*) on the affinity selector (S*) to electrostatic or hydrophobic adsorption, electrophoresis or even a size based separation; all of which will be described below. An essential feature in this dimension of analysis is that complexes must be partially or totally resolved in some way from the rest of the solution. Achieving this step by adsorption is illustrated in formula 2 below, wherein a matrix (M) surface adsorbs the S*:A complex as it passes.

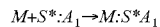

Formula 2

This step can be achieved in many ways. Ideally, the matrix is of high specific surface area (area/unit volume) and the distances at any point in the solution to the surface are 10 um or less. The surface of the matrix should also be rich in functional groups that react readily with derivatizing agents to allow covalent attachment of reagents such as some type of binding agent that targets the tag (*) on the affinity selector. The nature of these binding agents is described below. Examples of matrices are silica and organic resin particles used in chromatography columns to support stationary phases and monolithic chromatography columns. Chromatography particles with desirable properties will be <20 um in size, have pores of about 100 to about 500 nm in size, and a surface area exceeding about 40 m$^2$/mL. The material in a monolith will be silica or organic resin with through pores of <10 um and a second set of pores between about 100 and about 500 nm.

The symbol (*) on S* indicates a unique structural feature of either the affinity selector or complex that may be exploited in binding it to a sorbent matrix. The feature may be a structure element in S* alone or a new feature created as a result of S*:A complex formation. This unique structural feature can occur in S naturally or it can be chemically conjugated to S as a tag. An example of a natural feature would be amino acid sequences in a mouse, rat, rabbit, bovine, porcine, or equine antibodies that are uniquely different than those found in human immunoglobulins. Using an anti-mouse IgG immunosorbent attached to the matrix M would make it possible to select mouse antibodies from human plasma along with the antigens to which they have formed complexes.

In certain embodiments, semi natural tags can be added through genetic engineering that would allow the generation of amino acid sequence tags during expression of a polypeptide affinity selector. One such example in accordance with this aspect of the invention is a single chain antibody with an added peptide tail.

In accordance with other aspects of the present invention, affinity selectors can be extracted from samples either alone or with analytes to which they have complexed by covalently attaching a biotin, a hapten, a highly charged group, or an oligonucleotide tag to a selector (S*). In terms of the oligonucleotide tags, it should be understood and appreciated herein that it is possible to individually tag large numbers of different affinity selectors if desired.

In further aspects of the present invention, the affinity selectors can be separated from the analytes by one or more of the following non-limiting techniques: separating the analytes or formed immune complexes according to their hydrodynamic volume, adsorbing and differentially eluting the analytes from a hydrophobic surface, targeting a unique structural feature of the affinity selectors or the analytes to capture antibodies of the analytes or formed immune complexes, hybridizing oligonucleotides, capturing biotinylated affinity selectors with immobilized avidin, adsorbing and differentially eluting the analytes from a charged surface, adsorbing and differentially eluting the analytes from an immobilized metal affinity chelator, and adsorbing and differentially eluting the analytes from a boronic acid rich surface.

In another non-limiting example in accordance with the teachings of the present invention, anti-antibody immunosorbent media is used to capture mouse or rabbit antibodies that have been added to human plasma samples. During the course of recapturing these antibodies from the samples, any substance with which they had formed a complex will also be captured as well. After capturing the S*A complex, extensive washing of the surface bound complex is used to remove all other weakly bound components from the sample. This technique can be referred to more generally as the anti-affinity selector approach. In accordance with this illustrative embodiment, it should be understood that an antibody targeting any type of affinity selector can be used to pull complexes out of samples.

In terms of samples that do not contain large amounts of immunoglobulins, protein A, protein G and/or some other immobilized, antibody targeting protein can be used to isolate S*:A complexes in which S* is an immunoglobulin. This method is very similar to the anti-antibody strategy discussed above.

In accordance with another non-limiting example of the present invention, avidin sorbents are used to select biotin tagged affinity selectors and their complexes back out of samples. Again, extensive washing is used to remove substances from the sample that bind with low affinity.

It is envisioned that affinity selectors could also be tagged with a hapten for which an antibody has been prepared. When this hapten targeting antibody is immobilized, a second dimension capture matrix is used in the isolation of S*:A complexes. Moreover, when the affinity selector is an aptamer it can be selected from samples through the use of an oligonucleotide sequence immobilized on a second dimension matrix (M). The sequence on the aptamer targeted by the immobilized sequence is not used in complex formation and must be free to hybridize with the complementary sequence on the sorbent surface.

Affinity selectors tagged with DNA, RNA, or peptide nucleic acid (PNA) oligomers will be capable of binding to a complementary DNA, RNA, or PNA sequence on the matrix M through base pair hybridization. Each affinity selector (such as an antibody) is tagged (coded) individually or in groups with a unique DNA sequence of 8-12 bases. In addition, each coded affinity selector that contacts M to which a complementary oligonucleotide sequence has been attached will bind by hybridization, while complementary DNA sequences immobilized on the sorbent can either be distributed homogeneously or spatially grouped, depending on the manner in which they will be eluted. Complementary oligonucleotides are placed at different locations in a column when eluted sequentially by either denaturing the complex, dissociating the complementary hybrid, or both. When they are grouped together, a more elaborate sequential release procedure must be used involving thermocycling.

In terms of size, the matrix shows differential permeability to the S*:A complex instead of adsorbing it. After a small analyte has been complexed by a macromolecular affinity selector it behaves as a macromolecule, allowing it to be separated from other small molecules in the solution by a size discriminating separator such as a size exclusion chromatography (SEC) matrix, restricted access media (RAM), or semipermeable surface (SPS) media, field flow fractionation (FFF), hydrodynamic chromatography (HDC), or a membrane filtration system. The macromolecular S*:A complexes will have a much higher molecular weight than the low molecular weight components in samples and will be easily differentiated by size separating systems, including restricted access media (RAM) and semipermeable surface (SPS) columns. Low molecular weight, hydrophobic substances entering the pores or the semipermeable surface of these media would be differentially adsorbed. This means the RAM and SPS columns are separating molecules by both a size and hydrophobic interaction mechanism.

Figure 2:
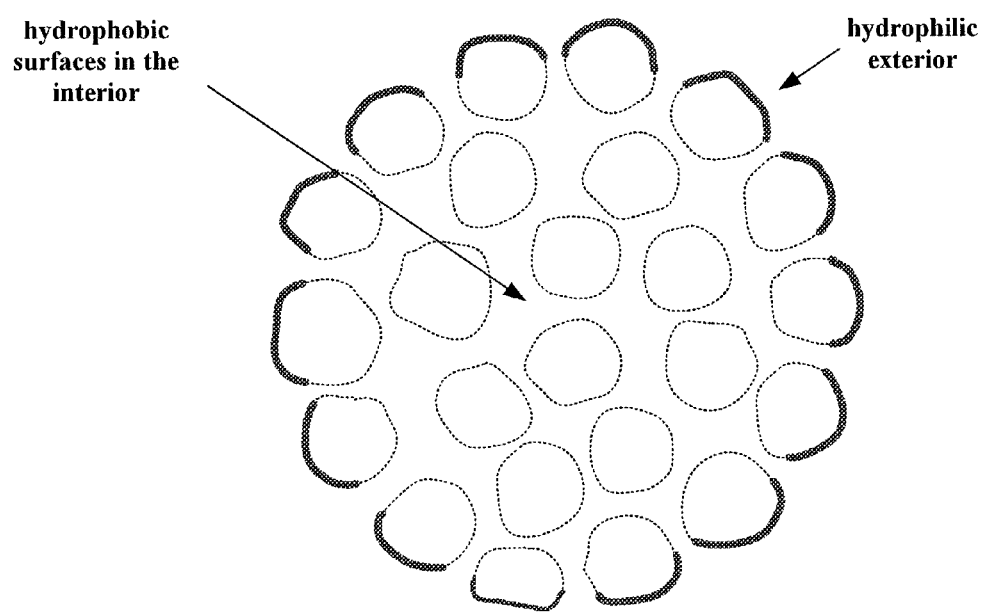
FIG. 2 is a restricted access media (RAM) particle in accordance with the teachings of the present invention.

Moving now to FIG. 2, an illustration of a restricted access media (RAM) particle is shown. In accordance with this illustration, RAM supports are generally an aggregate of submicron silica particles in which the interior surfaces of the support are covalently derivatized with stearic acid and the exterior surfaces of the support are derivatized with a glycerol ether of the structure —OCH$_2$—CH(OH)—CH$_2$OH. The average pore diameter between the submicron particles is about 6 nm on the average, which precludes entry of most proteins exceeding between about 20 to about 40 kD in molecular weight. In contrast, peptides and haptens of less than about 3 kD readily enter the interior of a RAM support where they are adsorbed from water.

Electrophoretic separations of complexes can be achieved by either differences in electrophoretic mobility or isoelectric point. In accordance with certain exemplary embodiments, it is desirable that the electrophoretic properties of the affinity selector be very different than those of the other species in the solution. While this would generally be true of DNA or RNA based selectors relative to the proteins in the solution, peptides and proteins in a complex with DNA or RNA could also be easily separated from other peptides and proteins in the solution as well.

Field flow fractionation (FFF) separates molecules differing in size by a mechanism that exploits size-related differences in their diffusion coefficients. HDC separates macromolecules by a slightly different mechanism that also produces size related differences in elution properties.

Figure 3:
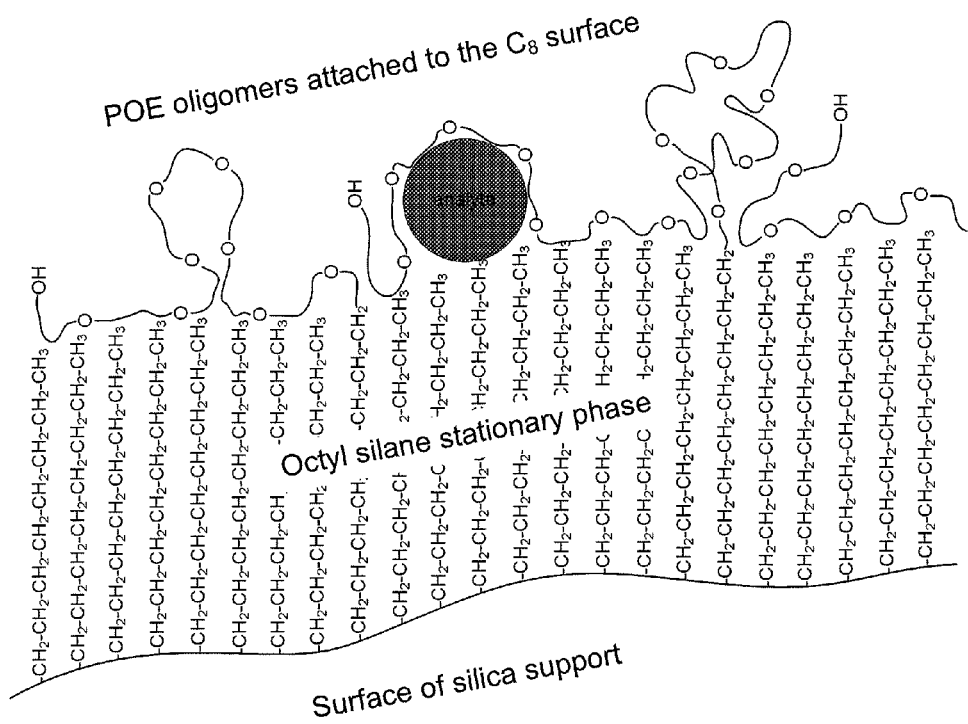
FIG. 3 is an illustration of a semipermeable surface (SPS) support in accordance with the teachings of the present invention.

In FIG. 3, an illustration of a semipermeable surface (SPS) support is provided. This sorbent is prepared by attaching a 300 dalton polyoxyethylene (POE) oligomer to an average of 1 in every 15 octyl ($C_8$) silane groups attached to the surface of a silica support. The POE oligomer associates weakly with the $C_8$ residues on the sorbent surface, blocking contact with proteins. Haptens and peptide in contrast can penetrate this coating and bind to the $C_8$ groups through a hydrophobic interaction mechanism.

The final component of the second dimension separation process requires that either the S*:A complex or the analyte alone be released from a sorbent in the second dimension and/or transported into the third dimension for further analysis. In the case of size selection of SEC, RAM, SPS, or FFF separations, the analyte can either be transported directly into the third dimension or the complex dissociated before the analyte is transported into the third dimension. Dissociation in the case of molecular sizing separations can be achieved by adjusting the pH at the exit from the molecular sizing column with a relatively acidic (pH 2.5) or basic (pH 12) mobile phase. Moreover, dissociation of immune complexes from immunosorbents is achieved either by relatively acidic (pH 2.5) or basic (pH 12) conditions. In addition to dissociating the Ab:Ab complex, Ab:Ag complexes are dissociated as well.

Biotinylated affinity selector:analyte complexes can be released from a mono-avidin affinity column in several ways. One is by adding biotin to the solution above the capture agent or to the mobile phase in the case of chromatography columns. This will release the biotinylated S*A complex. Mono-avidin columns can be used for many cycles when eluted in this manner. An alternative elution strategy is to apply an acidic solution having a pH of about 2.5. This will reversibly denature mono-avidin and release both the affinity selector and probably the analyte from the affinity selector. Moreover, other types of S*:A affinity selectors that are proteins can be dissociated from S* capture selectors in much the same way (i.e. with acidic solutions in the range of pH 2 to 2.5), and the analyte will generally be released at the same time.

In accordance with certain aspects of the present invention, the affinity selector can be a polynucleotide or have a covalently attached oligonucleotide. In accordance with this aspect of the present invention, complementary oligonucleotide sequences on some type of sorbent matrix ($M_{DNA}$ or $M_{RNA}$ in the formula above) are used to adsorb the S*:A complex from the sample. Dissociation and/or release of the complex or the components of the complex from $M_{DNA}$ is achieved with eluents that i) are of low ionic strength, ii) are very basic, or iii) contain a denaturant. Dissociation and release can also be obtained by elevating the temperature to melt the DNA:DNA, RNA:RNA, DNA:RNA, PNA:DNA, or PNA:PNA hybrid. Still another way would be to add a solution in the dissociation step that contains the same DNA (or RNA) sequence as in the tag on the affinity selector and then stopping the flow of the reagent across the surface of M. After flow is arrested, temperature of the solution is elevated to the point that the DNA:DNA, RNA:RNA, or DNA:RNA hybrid is melted. Thereafter, the temperature is allowed to return to room temperature so that rehybridization can occur. When the concentration of the complementary oligonucleotide added is high, it will out-compete the oligonucleotide tag on the S*:A complex, thereby leaving it in solution. The released complex may then be transported into the second dimension for further analysis.

Analysis in the third dimension in accordance with the teachings of the present invention depends on the ultimate detection method to be used at the end of the analytical process, as well as whether the analytes are i) small molecules such as haptens or peptides ii) proteins, glycoproteins, lipoproteins, polysaccharides, polynucleotides, or iii) some other macromolecular species. In terms of small molecules (i.e., haptens and peptides), when analytes are identified and quantified by electrospray ionization mass spectrometry (ESI-MS) or matrix assisted laser desorption ionization mass spectrometry (MALDI-MS), detection is more easily achieved if the analytes have a molecular weight less than about 2 kD. Larger molecules, on the other hand, can be detected as shown in FIG. 4; however, it should be noted that ionization efficiency is often higher with smaller molecules.

Figure 4:
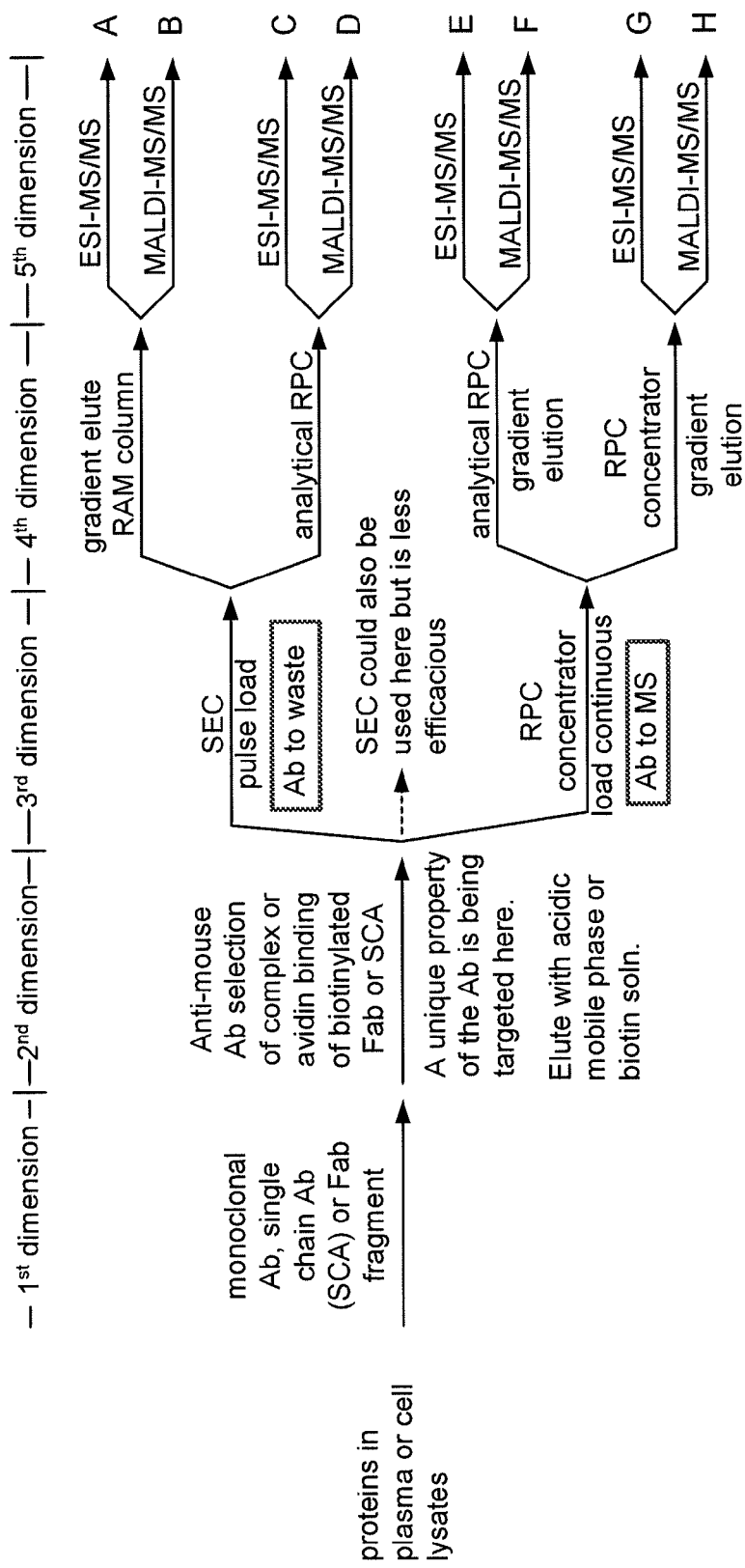
FIG. 4 is an analytical protocol for direct mass spectrometry (MS) analysis of proteins captured from a complex sample matrix by an affinity selector in accordance with the teachings of the present invention.

FIG. 4 is a multi-dimensional "analysis option tree" (AOT) for the analysis of proteins beginning with affinity selector binding of analytes in solution. Proceeding on from affinity complex formation, in accordance with certain embodiments of the present invention, the number of options for analysis can increase to eight, or even more by the fifth dimension of analysis. AOTs generally begin with affinity selection in the first dimension, proceed on through a series of chromatographic and/or chemical modification steps in the intermediate dimensions of analysis, and conclude with detection by mass spectrometry, fluorescence, or electrochemical means. The type of analyte being detected, sensitivity requirements, and available instrumentation dictate the branch of the tree taken for analysis.

An AOT for direct MS analysis of proteins sequestered from a complex sample matrix by some type of affinity selector, generally an antibody, Fab fragment of an antibody, single chain antibody, or phage display protein is seen in FIG. 4. After the intermolecular affinity selector:analyte complex is captured from the solution in the second dimension by a sorbent targeting the affinity selector, the anti-selector:selector:analyte complex is dissociated and the components further fractionated by either size exclusion chromatography (SEC) or reversed phase chromatography (RPC) in dimensions 3 and 4 before being sent to either an ESI-MS/MS or MALDI-MS/MS for direct analysis of the intact protein. To this end, it should be understood and appreciated herein that it can be helpful to convert proteins, glycoproteins, and lipoproteins to mixtures of peptides to identify and quantify them by mass spectrometry. This approach will be described below.

The outer branches of AOT for direct analysis of protein in FIG. 4 shows that the final choice is detection by either electrospray ionization (ESI) or matrix assisted laser desorption ionization (MALDI) mass spectrometry (MS). The choice between these two depends to a large extent on the instrumentation available and complexity of the sample. With complex mixtures, MALDI-MS may be a particularly useful option, particularly as MALDI-MS generally provides single charge states of a protein or peptide, thereby making it possible to examine 5-20 polypeptides (or even hundreds of species) at a time. ESI-MS, on the other hand, more frequently produces multiple charge states of a polypeptide that require a deconvolution algorithm to recognize the molecular weight of a protein. Although the molecular weights of proteins in a mixture may be different, multiple charge states of the protein fall in the same mass-to-charge ratio of the MS spectrum. The algorithm is generally unable to handle more than two proteins simultaneously. Another problem with ESI-MS detection of proteins is that distribution of the protein across multiple charge states reduces detection sensitivity. It should be noted that while detection is possible with ESI-MS, it is often best done with MALDI-MS.

Another element of the AOT is whether the affinity selector (Ab) will be removed from samples in dimension 3 before they are sent to the MS or left in the sample. Still referring to FIG. 4, while antibodies are removed in analytical routes A, B, C, and D, they are left in the samples of routes E, F, G, and H. As should be understood and appreciated herein, whether antibodies are removed from samples before the analysis depends on several issues. For instance, as antibodies are typically at least about 160 kD in size, when the molecular weight of the analytes is <100 kD a MALDI-MS analysis would have no problem differentiating between the two. A non-limiting advantage of MALDI-MS/MS is that it identifies primarily only the molecular ion and is able to differentiate between multiple protein species simultaneously on the basis of their differing molecular weight. This is particularly useful when examining a small number of antigens where the total concentration of antibody would probably be no more than ten times greater than antigen concentration. With large numbers of antigens, the total antibody concentration could be one hundred times larger than antigen concentration. Moreover, large amounts of antibody could potentially suppress ionization of low abundance antigens. The presence of antibody in samples would be more problematic in the ESI-MS mode of detection where multiple charging would cause ions from the antibody to overlap ions from antigens. With simple samples this mode of detection is certainly possible; however, as sample complexity increases, ESI-MS becomes less useful as a detection option.

With antibodies being 160 kD or larger in molecular weight, SEC on a 100-150 angstrom pore diameter column readily separate antigens of 80 kD or less from antibodies in the $3^{rd}$ dimension of routes A, B, C, and D of FIG. 4. Antibodies elute at or near the exclusion volume and are sent to waste. Antigens are directly transferred to chromatography columns having hydrophobic surfaces where they are captured and reconcentrated. When it has been decided that antibodies will be sent to the MS along with antigens, the two species are co-captured and fractionated by hydrophobic chromatography matrices in the $3^{rd}$ and $4^{th}$ dimensions of routes E, F, G, and H. The options in the $4^{th}$ dimension are whether a high resolution, gradient eluted analytical column is needed in routes E and F or whether a short, low resolution column would suffice as in routes G and H. When large numbers of analytes are being fractionation, routes E and F would be chosen. With small numbers of analytes, routes G and H are likely used.

Recent successes in proteomics are based on the fact that proteins are reduced to more easily identifiable fragments by cleavage with proteolytic enzymes, the most popular being trypsin (see Formula 3 below). Trypsin digestion is most widely achieved by incubating the protein mixture with a 50:1 mass ratio of protein:trypsin for a 24 hour period. At the end of proteolysis, the peptides generated will be analyzed in a manner similar to, or identical to, samples starting with peptide components. When more trypsin is used per mass of protein, trypsin begins to autodigest, thereby contaminating the sample with trypsin fragments.

Formula 3

It should be understood and appreciated herein that proteolysis is greatly accelerated by using trypsin immobilized on high surface area chromatography particles or monolithic media of the type described above. Moreover, protein samples are often forced through an immobilized trypsin bed in the manner an analyte is chromatographed. In this particular case, it is possible to use more trypsin than protein, particularly as trypsin is immobilized and thereby cannot autodigest.

Figure 5:
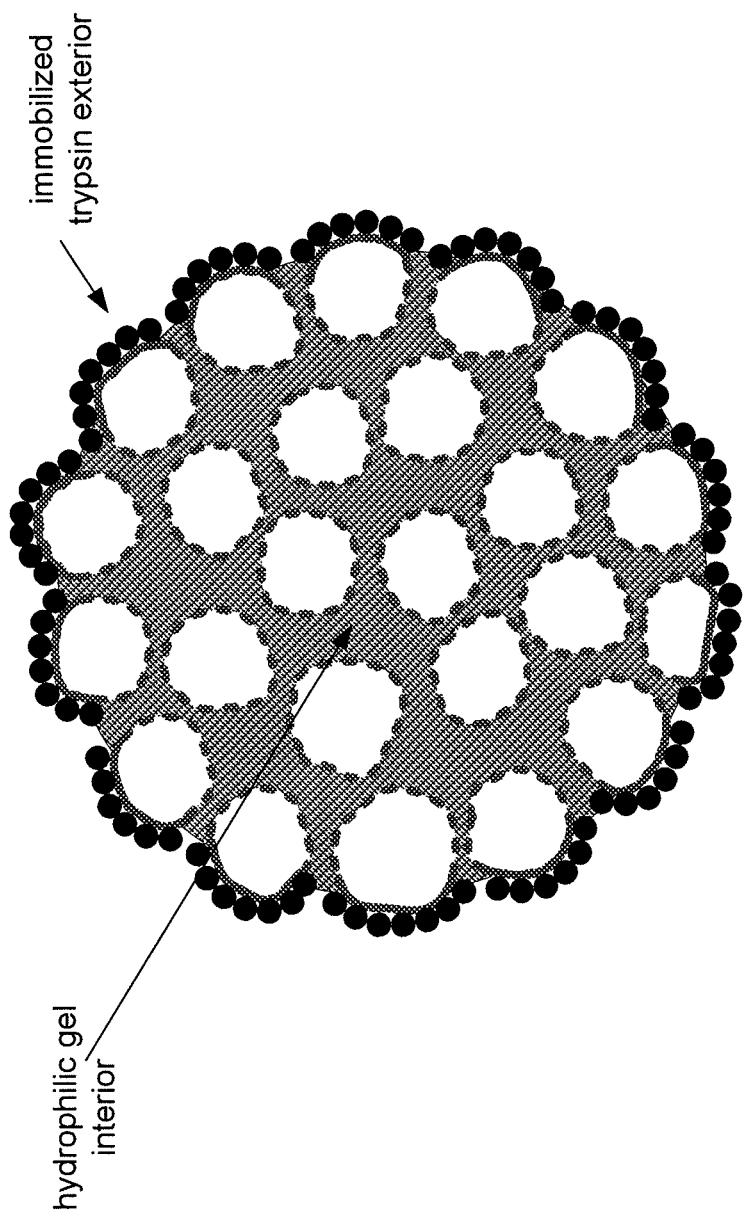
FIG. 5 is an illustration of a restricted access column in which the interior is a hydrophilic gel and the exterior is coated with immobilized trypsin in accordance with the teachings of the present invention.

As is shown in FIG. 5, immobilized trypsin can also be used in a chromatography column, but in a different manner than previously described. In accordance with certain aspects of the invention, the pH optimum of trypsin is in a pH range of from about 7 to about 9. Moreover, the catalytic efficiency with most proteins decreases a million fold when going to a pH in the range of from about 2 to about 3. Moreover, when proteins are eluted from second dimension capture columns with a mobile phase pH of approximately 2.5 and pass directly into trypsin columns the proteins will be in a solution that is too acidic for the trypsin to function. As such, the pH must be adjusted to about 8 by some type of buffer exchange before trypsin digestion will occur. This is accomplished by transporting the mixture of proteins and acidic elution buffer through a chromatographic matrix in which the outer surface of particles is coated with covalently immobilized trypsin and the pores are so small that molecules exceeding 20 kD can not penetrate but buffers freely enter the pore matrix of the particles. This size excluding column is filled with trypsin digestion buffer. As protein samples are transported through the column, proteins readily move ahead of acidic elution buffer into the trypsin digestion buffer where proteolysis begins to occur. With proteolysis, peptides are formed that can enter the pores of the restricted access column, but they and their protein parents have moved beyond the acidic elution buffer.

FIG. 5 shows an illustration of a restricted access column in which the interior is a hydrophilic gel and the exterior is coated with immobilized trypsin. The pore diameter of these particles is in the range of 6 nm or less. This column serves the function of achieving buffer exchange and proteolysis in the same operation. When a sample in acidic buffer is introduced into a column packed with these particles, protein in the sample is precluded from entering the pores and migrates ahead of the buffer entering the pores of the particles. Proteins migrate into a region in the column filled with a buffer suitable for proteolysis. At this point, proteolysis is catalyzed by trypsin covalently coupled to the particles.

Figure 6:
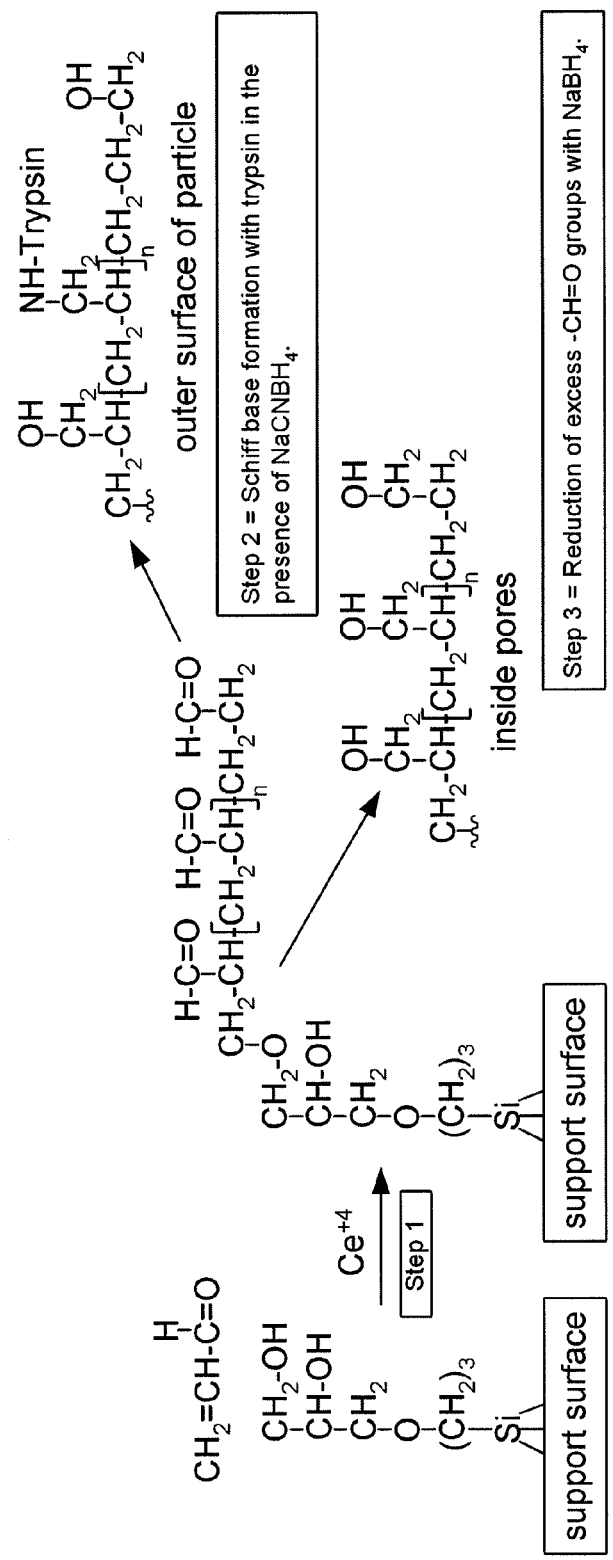
FIG. 6 depicts the synthesis of the coating involved in the trypsin-RAM column in accordance with the teachings of the present invention.

When trypsin is immobilized on a porous particle medium ranging from 6 to 30 nm, the column also functions as a size exclusion column. The pores are of a size that will partially exclude many proteins from penetrating the immobilized enzyme matrix. Starting with 6 nm pore diameter silica particles, these particles are coated with gamma-glycidoxypropyl trimethoxysilane and the attached oxirane hydrolyzed to yield a diol. Acrolein will be polymerized onto the diol matrix through $Ce^{+4}$ catalysis to yield the poly(aldehyde) matrix shown in FIG. 6, Step 1. The poly(aldehyde) then partially fills the pores of the silica support matrix and the trypsin is brought into contact with the particles where lysine residues on the enzyme will covalently attach to the silica matrix through Schiff base formation in the presence of sodium cyanoborohydride (Step 2 in FIG. 6). $NaCNBH_4$ added to the reaction mixture reduces Schiff bases as they are formed but does not reduce aldehydes. The pores of the support matrix are so small that trypsin can only gain access to aldehyde groups on the exterior of the particle. In other words, there will be no trypsin in the pores of the particle. After trypsin immobilization and aldehyde residues (—C═O) on the particles will be reduced with $NaBH_4$ (Step 3 of FIG. 6) thereby completing the synthesis of the immobilized enzyme matrix.

In addition to having trypsin on the exterior of the particle, the exclusion of proteins (and to a large extent, peptides) from the pores of the particle are both unique features of the present inventive matrices. This means that when an immobilized enzyme column is prefilled with a buffer having a pH of approximately 8 and connected in series with, for example, an anti-mouse Ab column that has a selected Ab:Ag complex in which the Ag is a protein or an avidin column that has selected a biotinylated Ab:Ag complex in which the Ag is a protein and is being eluted with a pulse of pH 2.5 eluent: 1) the acidic mobile phase will enter the pores of the immobilized enzyme column while 2) all proteins will be excluded and moved far ahead of the acid, and 3) as part of the exclusion process move into pH 8 buffer. Residence time of proteins in the immobilized enzyme column is controlled by either the flow rate through the column or by interrupting flow through the column at some point after proteins have entered the immobilized enzyme column and before they exit. This column will generally be used in the $3^{rd}$ dimension of analysis as seen in FIG. 7.

Figure 7:
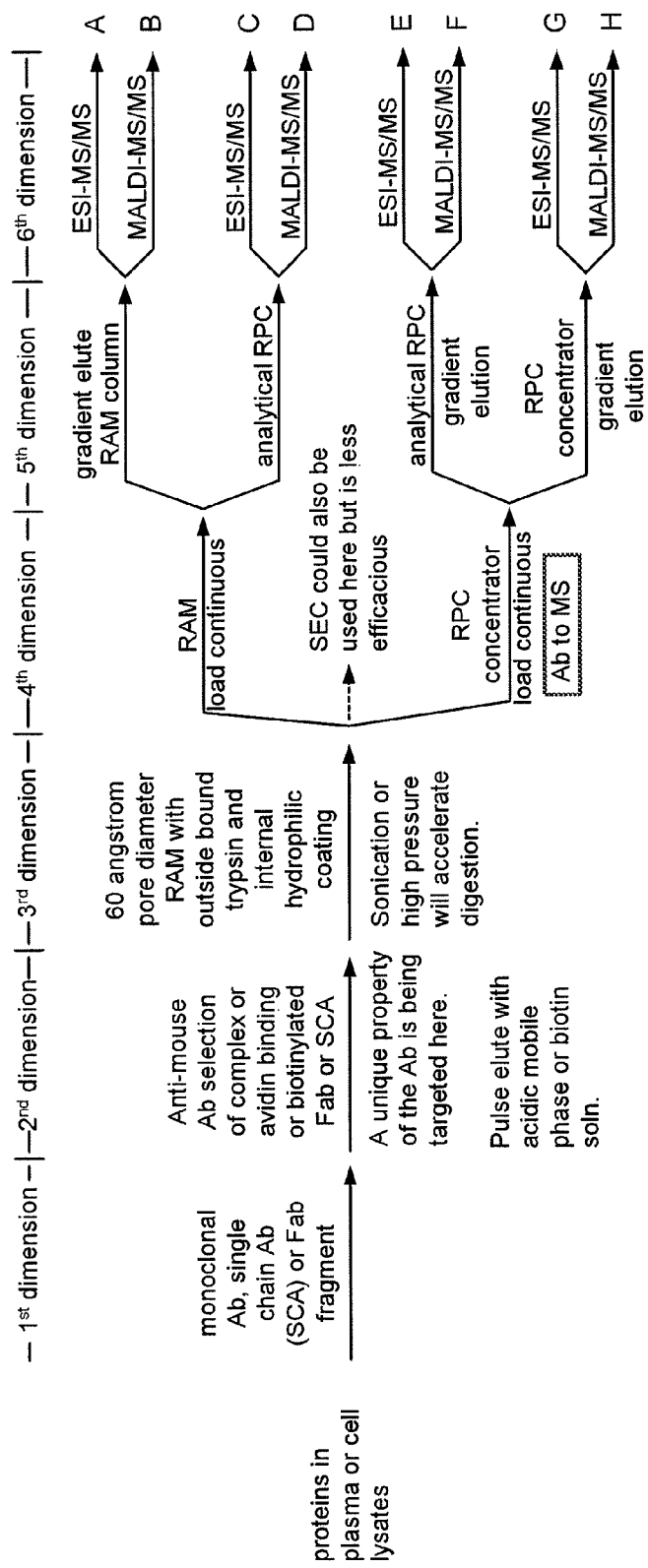
FIG. 7 is an analytical protocol for a mass spectrometry analysis of proteins captured from a complex sample matrix by an affinity selector and then subjected to proteolytic digestion before further analysis in accordance with the teachings of the present invention.

In contrast to FIG. 4, which showed the selection and analysis of protein at the whole protein level, FIG. 7 shows the capture and isolation of intact proteins from mixtures after which they are converted to peptides for identification and quantification by mass spectrometry. Immune complexes are again isolated from samples and enriched on an immunosorbent that targets epitopes unique to the antigen targeting antibody or on an affinity sorbent targeting a tag on the capture antibody. After washing to remove substances bound to complexes with low affinity, non-covalent complexes are dissociated with an acidic (~pH 2.5) mobile phase and antigens along with the capture antibody are transported to the immobilized trypsin column. As the proteins and acidic buffer pass through this column they are resolved as proteins migrate into a trypsin digestion buffer. During this process, proteins are converted to peptide cleavage fragments in the $3^{rd}$ dimension of analysis. These fragments are reconcentrated in the $4^{th}$ dimension, further resolved by some type of hydrophobic interaction chromatography, and then finally identified and quantified by either ESI-MS/MS or MALDI-MS/MS. Proteins generally yield thirty to several hundred peptide fragments, any one of which can be used to identify and quantify a protein parent. Peptides chosen for identification and quantification are generally those that have high ionization efficiency, provide a sequence that is unique to the parent protein, and are well retained by reversed phase chromatography columns.

The rationale for the type of mass spectrometry to use is different with peptides than was the case with proteins in FIG. 4. In this case, it is possible to fragment peptides from the first dimension of mass analysis by either collision induced dissociation (CID), electron transfer dissociation (ETD), or some other method that fragments gas phase ions from the first dimension of MS analysis. CID and/or ETD fragment ions are then resolved and recorded in a second dimension of mass analysis. This three dimensional process provides a sequence bearing signature unique to each peptide. An extremely attractive feature of this approach is that the MS data can be directly tied to sequences in DNA databases, allowing the identification of genes and parent proteins from which peptides were derived. ESI-MS/MS and MALDI-MS/MS are more comparable in capability in this case. With either approach, it is possible to identify hundreds of peptides in a single analysis. Because suppression of ionization occurs by different mechanisms in MALDI-MS and ESI-MS, some peptides are detected better with some types of MS more than others.

Figure 8:
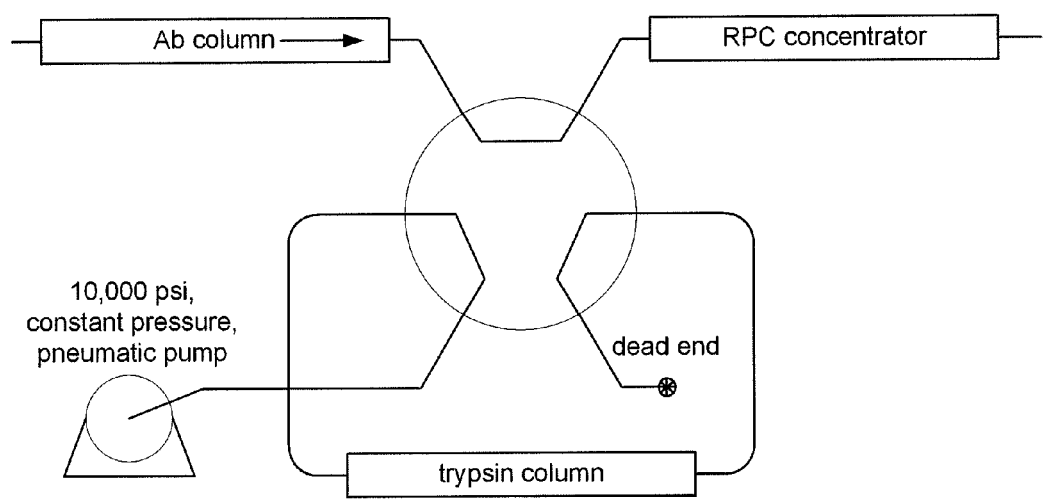
FIG. 8 is an exemplary valving system that allows high pressure to be applied to an immobilized enzyme column in the stopped flow mode of analysis in accordance with the teachings of the present invention.

It should be understood and appreciated herein that the rate of proteolysis in the immobilized enzyme column can be accelerated by raising the temperature, by sonication, or by increasing the pressure inside the column to ~10,000 psi. An exemplary set-up for increasing the pressure in this respect is illustrated in FIG. 8, which specifically shows a valving system that allows high pressure to be applied to an immobilized enzyme column in the stopped flow mode of analysis. In accordance with this illustration, high pressure is thought to facilitate proteolysis by the partial denaturation of proteins. Proteolysis of a sample begins by switching the valve into a position such that the immunosorbent, trypsin column, and RPC concentrator are connected in series. In this position, proteins are desorbed from the Ab column and transferred into the trypsin column where the desorbing buffer and proteins are separated by a size exclusion mechanism. At this point the valve is switched into a position that arrests the flow of mobile phase through the column, thereby bringing the trypsin column into a high pressure incubation mode. After proteolysis, the trypsin column is switched back to the loading position and the digested protein mixture is transported to the RPC concentrator.

The immobilized enzyme column in FIG. 8 is in the $3^{rd}$ dimension of analysis in FIG. 7. Antigens and antibodies released from the affinity column in the $2^{nd}$ dimension of FIG. 7 are transported directly into the immobilized trypsin column in FIG. 8 where the acidic eluting buffer and proteins are separated as the protein migrates into the trypsin digestion buffer. Based on the volumes of the columns in the $2^{nd}$ and $3^{rd}$ dimensions, the amount of solvent that must be pumped through the system to cause this separation is calculated. When proteins have migrated halfway through the trypsin column, the valve is switched to the position indicted in FIG. 7. In this valve position, very high pressure from the pneumatic pump can be applied to the trypsin column at zero flow rates. Flow from the immunosorbent column directly to the RPC concentrator continues in this valve position. After about 1 to about 10 minutes of stopped flow in the trypsin column, the valve is rotated back to the position connecting the affinity capture column, the immobilized trypsin column and the RPC concentrator in series. The proteolytic digest from the trypsin column will then be transferred to the RPC concentrator.

Following proteolysis, peptides from proteins that will be identified and detected by mass spectrometry are examined by one of the procedures described in FIG. 7. To this end, dimensions 4 through 6 (as shown in FIG. 7) are the same as dimensions 3 through 5 for peptide analysis, the reason being that peptides are being examined in both cases.

According to certain aspects of the present invention, haptens and peptides are reconcentrated after their generation in the analytical process and/or after their separation from nonanalytes in the second dimension. This process, when it is carried out in a chromatography column, is often referred to as refocusing since analytes are adsorbed in a tight zone at the column inlet. Reconcentration and further separation of analytes can be achieved in multiple ways ranging from some form of affinity selection mechanism to ion exchange or hydrophilic interactions mechanisms, but a hydrophobic interaction mechanism is particularly useful because it is the most universal adsorption method, and at this stage, most analytes will be in water. Moreover, water is the most favorable solvent for adsorption with the hydrophobic interaction mechanism. Separations by hydrophobic interaction (reversed phase chromatography and RAM) are seen in the third and fourth dimensions.

Figure 9:
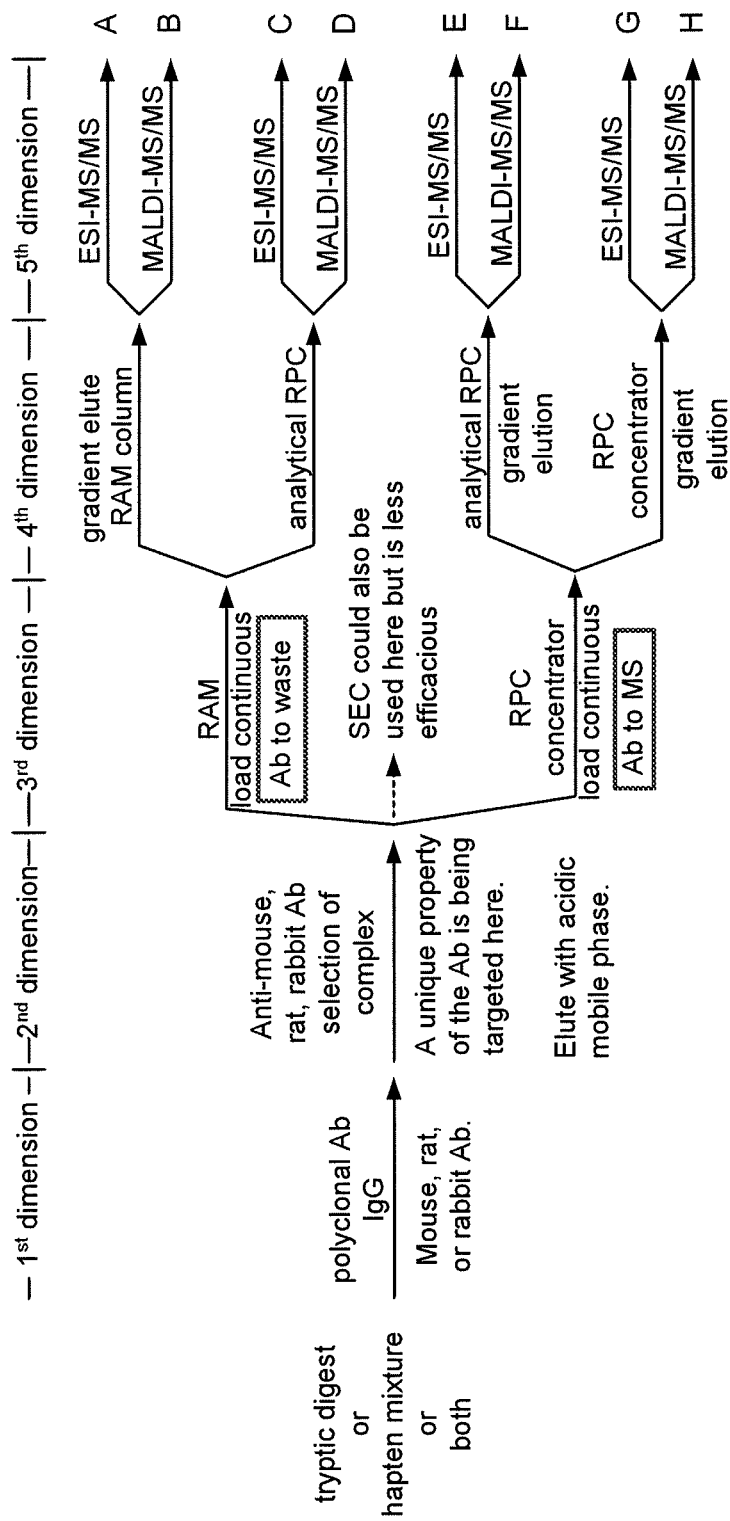
FIG. 9 is an illustration of a protocol used in the analysis of haptens and peptides captured by a polyclonal antibody affinity selector in accordance with the teachings of the present invention.
Figure 10:
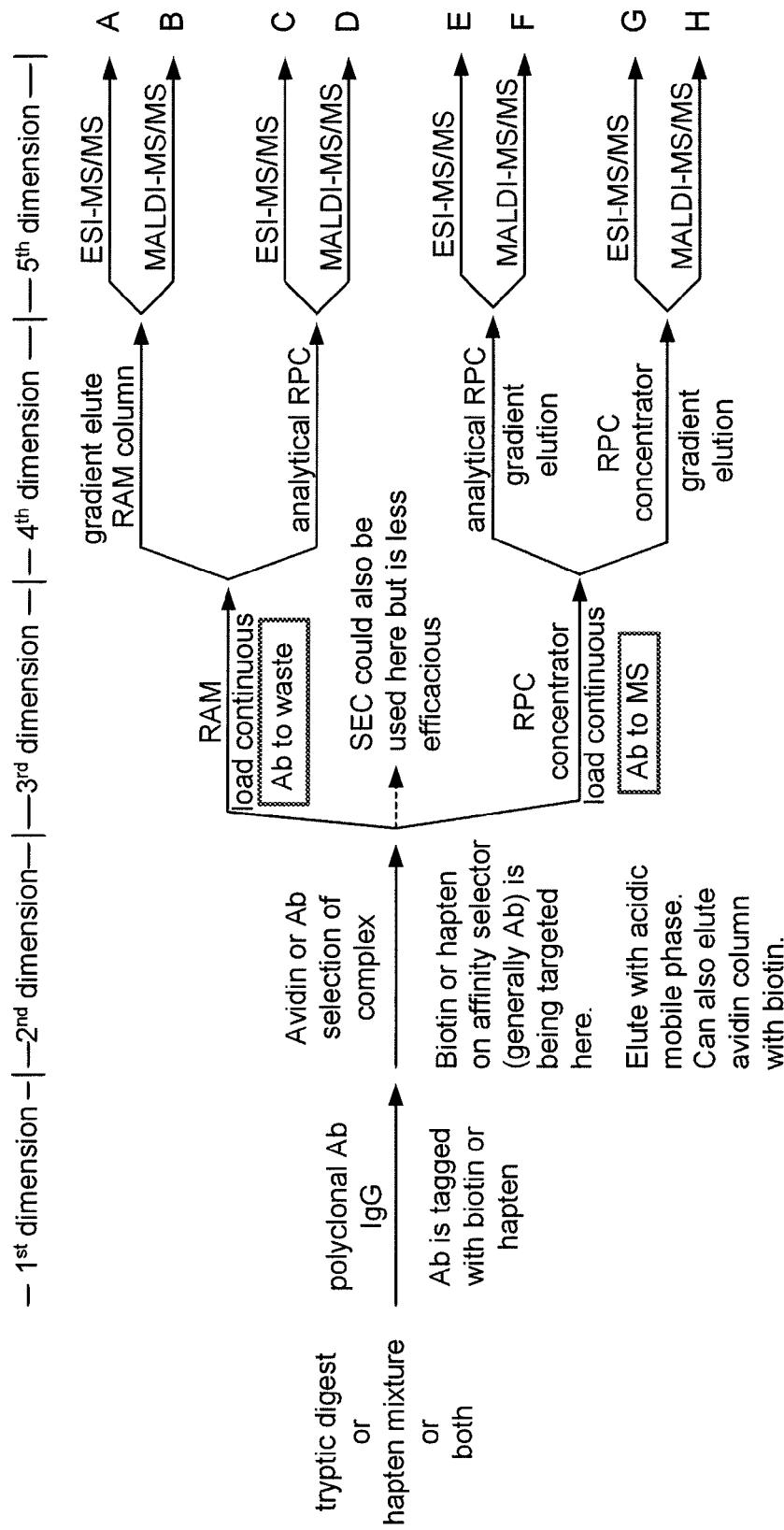
FIG. 10 is an illustration of a protocol used in the analysis of haptens and peptides captured by a biotinylated affinity selector in accordance with the teachings of the present invention.
Figure 11:
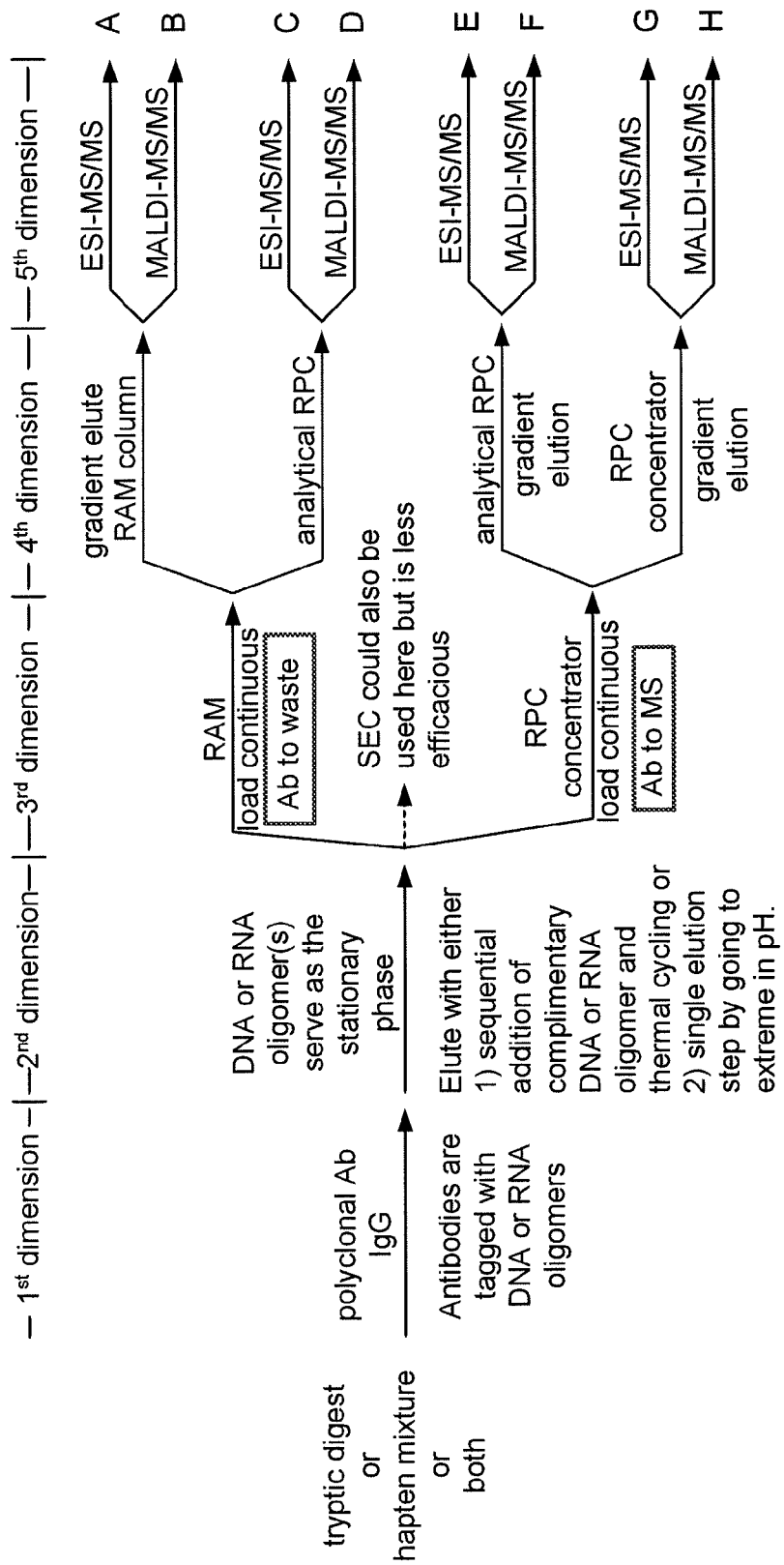
FIG. 11 is an illustration of a protocol used in the analysis of haptens and peptides captured by a DNA, RNA, or PNA affinity selector in accordance with the teachings of the present invention.

It should be understood and appreciated herein that the major difference between FIGS. 9, 10, and 11 are related to the manner in which the antibody used in complex formation is tagged and selected in dimensions 1 and 2. At the end of the first two dimensions, analytes are released from the selector (s) in a single group, or a small number of groups. There could be 10 to more than a thousand analytes in a group that must undergo further separation before they can be differentiated and detected individually. At least a portion of this separation is achieved with reversed phase chromatography.

Reconcentration of analytes released from affinity selectors were achieved in one of two types of affinity selector. One was the RAM (or SPS) column (FIG. 2). The advantage of this column is that it separates the affinity selector (generally an antibody) from haptens and peptides. Peptides and haptens penetrate into the pores of the RAM column or through the outer coating of the SPS column where they are adsorbed hydrophobically. Because the antibody is large, it cannot penetrate the pore or coating and is carried away to waste as indicated in FIGS. 8-10. An alternative concentrator is a short reversed phase chromatography column of ~1 cm in length. Haptens, peptides, and protein are all captured on the column, in addition to selector antibodies. Because samples are being refocused at the column inlet, there is no need for a sharp, small, discrete injection of samples. In addition, large sample volumes can be loaded continuously.

FIG. 9 is an illustration of the protocol used in the analysis of haptens and peptides captured by a polyclonal antibody affinity selector in accordance with the teachings of the present invention. In accordance with this aspect of the invention, haptens and peptides release from the affinity selector that captures immune complexes in the $2^{nd}$ dimension and are then refocused and further resolved by a RAM or RPC column prior to ESI-MS/MS or MALDI-MS/MS. Refocusing and reversed phase separation occurs in the $3^{rd}$ and $4^{th}$ dimensions of analysis. While it is possible to go directly from the $2^{nd}$ to the $4^{th}$ dimension, the RAM or RPC concentrator preserves the analytical column. It is also possible, in many cases, to separate the Ab used in the first dimension from analytes in the $3^{rd}$ dimension.

Release from the affinity selector in the $2^{nd}$ dimension is usually achieved with an acidic aqueous mobile phase. This mobile phase is ideal for adsorption of down stream RAM or RPC columns in the $3^{rd}$ dimension. Because analytes are refocused in the RAM or RPC column, large sample volumes may be used without adversely affecting resolution or the RAM or RPC columns in the $4^{th}$ dimension. The same logic and elution protocols in dimensions 2, 3, and 4 apply for FIG. 10.

One of the decisions in the analytical option tree shown in FIG. 9 is whether to use a RAM column or an RPC concentrator. While the RPC concentrator is simpler, has greater binding capacity, and is less expensive than a RAM column, RPC columns disadvantageously capture peptides, haptens, and antibodies. In addition, all antibody species elute together from RPC columns late in the chromatogram during gradient elution. This means that the antibody peaks will be large relative to analyte peaks. This is not a problem in most cases because peptides and haptens elute long before antibodies. The large antibody peak will not mask analyte peaks when this is true. When samples contain analytes that elute at roughly the same time or after antibodies, RPC columns cannot be used. In this case, a RAM column should be used. Antibodies are too large to penetrate the pores of RAM sorbents and pass through the column without adsorption, while peptides and haptens, in contrast, enter the pores of RAM sorbents and are captured in the hydrophobic interior of the particles.

When the hapten or peptide mixture is relatively simple, the RAM or RPC concentrator can be gradient eluted directly into the ESI-MS or onto the MALDI-MS analysis plate. The peak capacity of these short columns is often no more than 50 components. There is no need for a higher resolution separation column such as the "analytical RPC" column. This is shown as occurring in the fourth dimension in FIGS. 9-10, but it is the same column that was loaded with sample in the third dimension. In contrast, complex analyte mixtures will require much longer, higher resolution RPC columns. These analytical columns are from 10-50 cm in length and are packed with particles ranging from about 1.5 to about 5 um in diameter with an octadecyl silane (C18) coating. Analytical columns can have peak capacities of up to 600 components when slowly gradient eluted and heated to enhance mobile phase diffusion rates. Because substances are eluted from the RPC column into a mass spectrometer, coeluting peaks can be differentiated in either a first or second dimension of mass spectrometry.

The type of mass spectrometry used in the $5^{th}$ and higher dimensions depends on the complexity of the initial sample matrix, the number of analytes being analyzed, and analyte concentration. When the sample matrix is simple and fewer than 10 analytes are being examined, single dimension mass analysis of molecular weight alone in either the MALDI or ESI mode will be adequate. CID followed by further mass analysis of fragment ions in a $6^{th}$ and $7^{th}$ dimension allow higher confidence levels in identification but is probably not necessary. The type of mass spectrometer with simple samples is determined primarily on the basis of what is available when sample concentration is in the ug/mL to mg/mL range. Much higher sensitivity would be obtained in the ESI mode by using a mass spectrometer such as a triple-quadrupole (QQQ) or quadrupole-ion trap (Q-Trap) instrument in the selected ion monitoring mode. Instruments such as these, which mass analyze a particular ion for longer periods of time and accumulate greater numbers of ion counts for a specific analyte, can have a one hundred fold or greater sensitivity than rapid scanning instruments.

With very complex samples, the ESI-MS/MS instruments are particularly useful for the protocol of FIG. 9 because they provide a high level of discrimination. Again, when highest sensitivity is needed QQQ or Q-Trap type instruments provide the best solution.

The major difference between FIG. 9 and FIG. 10 is in the type of tag placed on selection antibodies and the manner in which immune complexes are captured. The antibody tag in FIG. 10 is either biotin or some hapten. FIG. 10 shows an illustration of the protocol used in the analysis of haptens and peptides captured by a biotinylated or hapten tagged affinity selectors. In accordance with this illustration, mono-avidin is used in the $2^{nd}$ dimension affinity selector because less severe conditions are required to release biotinylated species. Haptens and peptides can be released in the $2^{nd}$ dimension either by biospecific displacement or affinity selector denaturation.

The most gentle is with a biotin displacer. The disadvantage of this approach is that desorption kinetics are slow, requiring slow flow rates during the elution step. By contrast, partial denaturation with an acidic mobile phase, as described in FIG. 9, is much faster. Additional steps along the analytical option tree are identical to those described in FIG. 9.

FIG. 11, on the other hand, is an illustration of a protocol used in the analysis of haptens and peptides captured using antibodies tagged with a DNA, RNA, or PNA. As in other examples discussed above, separation of the immune complex from other substances in a sample occurs in the $2^{nd}$ dimension. Elution of captured antibodies from the $2^{nd}$ dimension occurs by raising column temperature above the melting point of the oligonucleotide hybrid. When thermocycling occurs under flow, all dissociated species are swept from the column. Thermocycling under arrested flow in the presence of competing oligonucleotides allows differential displacement of specific antibodies. Elution conditions in the $2^{nd}$ dimension are sufficiently mild that the immune complex may still be intact as it passes into the $3^{rd}$ dimension and is captured. When this is true the immune complex will dissociate in the $3^{rd}$ dimension as RPC or RAM columns are eluted with an acidic mobile phase containing acetonitrile. Whether the immune complex is intact or dissociated will not impact the net outcome of the analysis. The rest of the workflow is as described in FIG. 9.

With reference to FIG. 9, analytes are selected in the $1^{st}$ dimension by complexation with an affinity selector such as an antibody. The unique feature of the affinity selectors used in this case is that they are tagged with an oligonucleotide ($ONT_t$ composed of an ordered base sequence of RNA, DNA, or PNA. All the antibodies can have the same oligonucleotide sequence or each antibody species can be tagged with a different oligonucleotide sequence. Subsequent to complex formation in solution, the soluble complex is captured from samples by passing an aliquot of the solution through particles or across the surface of a solid support containing an immobilized oligonucleotide selector ($ONT_s$) with sequences complementary to those on the affinity selector. There will be one complementary oligonucleotide sequence on the solid phase surface for each nucleotide tag on an antibody. During the course of passing an aliquot of the solution across the oligonucleotide ($ONT_s$) bearing surface, analyte:selector-$ONT_t$ complexes will be captured by hybridization, forming a —$ONT_t$:$ONT_s$:selectoranalyte complex. Oligonucleotides (ONTO immobilized on the solid surface may be comingled or each can be located at spatially different sites. In accordance with certain specific embodiments, it is particularly useful that the support matrix for immobilizing $ONT_s$ is an organic resin, such as the pressure stable styrene-divinylbenzene resins used in HPLC. The POROS support matrices from Applied Biosystems are ideal examples of such resins. Advantageously, these resins withstand temperatures from about 80-90° C., as well as wide extremes in pH that may be used in analyte elution as described below.

Following the capture of analyte:selector complexes in the $2^{nd}$ dimension they must be released and eluted into the $3^{rd}$ dimension. The elution step can be achieved in several different ways in accordance with the teachings herein. One exemplary method is to dissociate the hybrid by raising the temperate of the solid phase adsorbent bearing the —$ONT_t$:$ONT_s$:selectoranalyte complex above the melting point of the —$ONT_t$:$ONT_s$ hybrid while the mobile phase is passing across the surface and being transported to the $3^{rd}$ dimension. The —$ONT_t$:$ONT_s$ hybrid will dissociate and the $ONT_s$:selector:analyte complex will be transported to the $3^{rd}$ dimension. In most cases, the $ONT_s$:selectoranalyte complex will remain intact, but in some cases it will partially or totally dissociate. Whichever the case may be will be accommodated in the $4^{th}$ dimension.

A second exemplary method of elution is to use extremes in either pH or ionic strength to dissociate the hybrids. When the solid phase adsorbents are eluted with distilled water, the —$ONT_t$:$ONT_s$ hybrid generally dissociates. Use of a pH 10 buffer at low ionic strength accomplishes the same thing.

Figure 12:
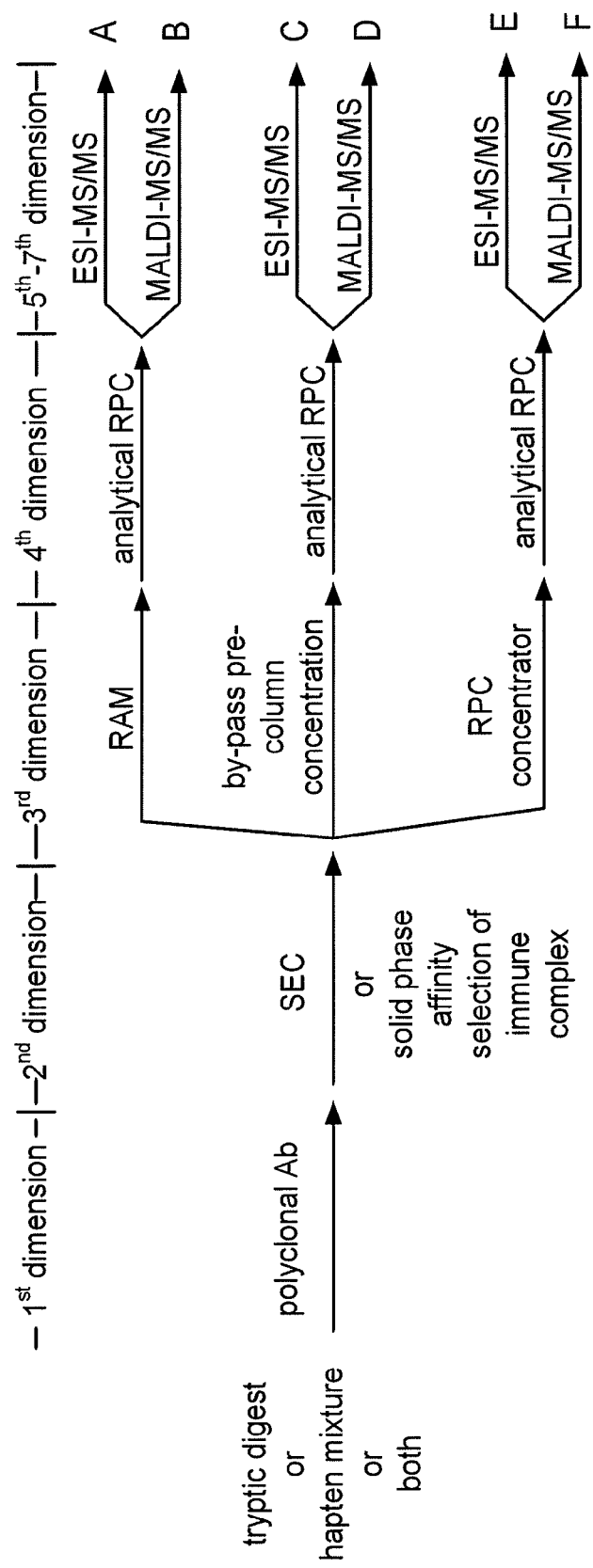
FIG. 12 is an illustration of a protocol used for fractionating immune complexes based on molecular size in accordance with the teachings of the present invention.

Immune complexes can also be fractionated according to molecular size (see FIG. 12). Immune complexes are fractionated in the $2^{nd}$ dimension in this workflow using size exclusion chromatography. The pore diameter of the SEC column is in the range of about 100 to about 150 angstrom while the particle size of the exclusion matrix should be about 3 to about 5 um. Immune complexes will elute near the exclusion volume of the column in the case of the 100 angstrom pore diameter packing material and are directly transported to the RPC or RAM concentration or directly to the analytical RPC column. At the conclusion of this transfer, lower molecular weight species eluting from the SEC column are diverted to waste. The RPC columns are eluted in a linear gradient with a mobile phase ranging from 0.1% trifluoroacetic acid or 1% formic acid to the same concentration of acid containing 70% acetonitrile. This mobile phase is sufficiently acidic to dissociate immune complexes captured at the inlet of the RPC columns. The rationale for which type of mass spectrometry to use is the same as in other cases.

Figure 13:
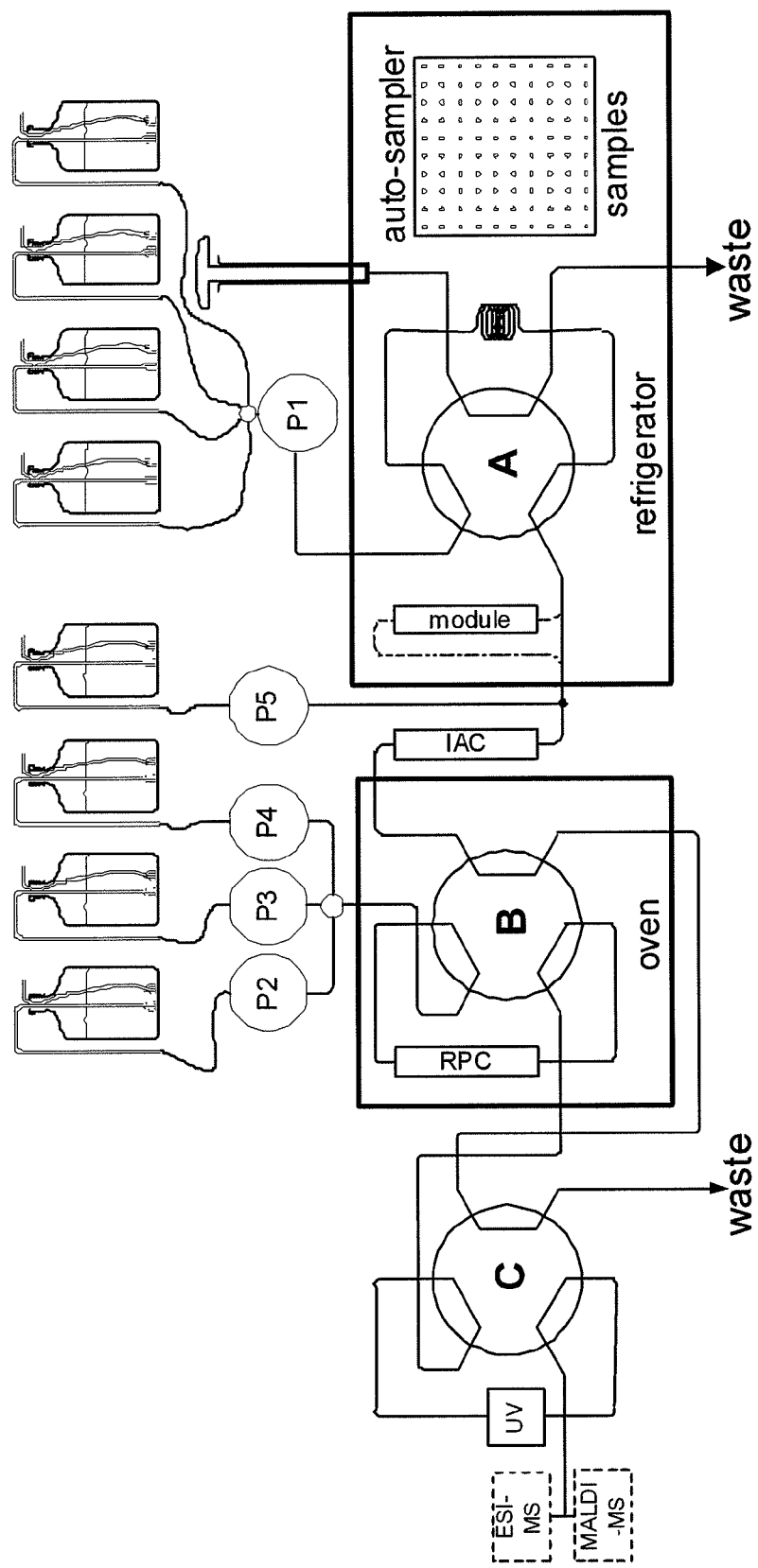
FIG. 13 is a liquid chromatography component of an instrument platform that is capable of carrying out a high resolution analysis of an affinity selector based process for simultaneously analyzing multiple analytes in accordance with the teachings of the present invention.

As noted above, proteins require the addition of a proteolytic dimension beyond that required in the analysis of haptens and peptides. This is generally achieved in the third dimension. FIG. 13 shows a liquid chromatography component of an instrument platform that is capable of providing the automated, high resolution separation of an affinity selector needed for high throughput and simultaneous analysis of multiple analytes. Sample preparation is initiated in an autosampler housed in a refrigerated chamber that minimizes microbial growth of a sample prior to analysis. Auto-sampler vials holding samples are of the conical bottom type to minimize sample volume. In addition to multiple samples, the auto-sampler also holds antibody solutions at a fixed concentration necessary for the analysis. The auto-sampler can also be loaded with additional reagents needed for reduction, alkylation, derivatization, proteolysis, internal standards addition, and diluents, any of which can be aliquoted into sample vials in any order. An analysis begins in the auto-sampler when a robotic syringe removes an aliquot of antibody, antibodies, or reagent from a reagent vial and adds them to a sample. Multiple reagents can be added sequentially to a sample vial as might be needed in reduction, alkylation, and proteolysis of a sample before analysis. A single antibody reagent vial may contain one antibody or all the antibodies necessary for a particular multiple analyte analysis. After dispensing a reagent or antibody into a sample the syringe goes to a vial in the auto-sampler containing reagent free buffer and is cleaned by fully loading the syringe with buffer multiple times and dispensing the buffer to a waste vial.

After an incubation time suitable to form a derivative and/or immune complex(es), the auto-sampler withdraws an aliquot of solution from a sample vial and loads a fixed volume sample loop on a high pressure valve in the sample loading position. The valve is then rotated to introduce the sample loop into a mobile phase flow path connecting it to a down stream column. The first down stream column (in the $2^{nd}$ dimension of analysis) is generally an affinity column or size exclusion column that will partially or totally resolve the immune complex(es) from other components in the sample. When the immune complex(es) are captured by an affinity column, it is desirable that 20 or more column volumes of mobile phase be pumped through the column to remove substances bound to the immune complexes or column with low affinity. When high binding affinity antibodies are used in the analysis, all other bound species will be non-analytes. This washing step thus removes non-analytes and is part of the separation process.

The column used in the second dimension of analysis can either be housed inside the refrigerated chamber of outside at room temperature as illustrated in FIG. 13. When using a high affinity antibody in the capture column, or an SEC column in the $2^{nd}$ dimension, the column is operated at room temperature. Lower temperature operation is used with affinity columns when the capture agent is of low affinity and the binding constant of the capture agent is increased by going to lower temperature. At 5° C. the binding constant can be double that at room temperature.

The illustration in FIG. 13 shows that analysis in the $3^{rd}$ and $4^{th}$ dimension can be carried out in an oven. The illustration shows direct transfer of analytes from the $2^{nd}$ dimension to the high resolution, analytical RPC column in the $4^{th}$ dimension in FIGS. 9, 10, and 11. In accordance with some embodiments, a $3^{rd}$ dimension column can be added before valve B. The function of a heating column in accordance with these embodiments is to diminish the limitations known in the liquid chromatography literature as mobile phase and stagnant mobile phase limitations. By reducing mobile phase viscosity and increasing the rate of analyte diffusion, resolution is increased in RPC. This increases the resolution of RPC columns and the number of analytes that can be resolved.

The first pump (P1) in the system in FIG. 13 provides solvents for the first two dimensions of separation. Solvent switching is done on the low pressure side of the pump, meaning that gradients generated with this pump are of the step gradient type. The pump P5 between the two chromatography systems is used to introduce mobile phases for dissociation of immune complex as would be needed when an SEC column would be used in the $2^{nd}$ dimension and a RAM column in the $3^{rd}$ dimension. The eluent stream leaving an SEC column would be merged with an acidic solution provided by P5 that would dissociate the complex before it reached a RAM column on valve B.

Valve C is used to uncouple chromatography columns from the detectors and preclude transport of undesirable reagents or analytes to detectors. For example, it was noted above that large amounts of antibody will accompany samples into the RPC column and will be eluted at the end of the mobile phase gradient after all the analytes. In accordance with this particular illustrative scenario, valve C can be switched to the position where the chromatography system is uncoupled from the MS and antibodies eluting from the RPC column are diverted to waste. A UV absorbance monitor is seen in the illustration, however, it should be understood and appreciated herein that it is not required and may be eliminated in certain embodiments. Moreover, redundant measurement devices can also be occasionally used to quantify analytes in multiple ways to validate accuracy of quantification.

Analytical optimization trees to this point have emphasized detection by mass spectrometry. When analytes leave the first 4 separation dimensions pure or such that the analyte is the only species in the eluent stream carrying a particular chromophore or electrochemically active functional group, it is possible to detect analytes in other ways, referred to below as non-MS detection modes. Examples of such non-MS detection modes include, but are not limited to, absorbance, fluorescence, or an electrochemical means.

With respect to the affinity selector based process, the simultaneous determination of multiple analytes to discriminate between analytes and a very large number of non-analytes through several dimensions of orthogonal analysis is important. Based on the very high level of selectivity afforded by antibodies, the first dimension of discrimination will generally be an affinity selector:analyte complex formation in solution. Most generally the affinity selector will be an antibody; however, it should be understood and appreciated herein that a variety of other selectors may be used as well. In addition, complex formation is executed in solution because it circumvents the need to immobilize large numbers of selectors and the inherent problems associated therewith.

The second, third, and often fourth dimensions of analysis discussed above have shown how several chromatographic methods, and often a chemical reaction, can be coupled to provide still higher levels of analyte discrimination. The resolving power of these dimensions is such that captured antigens can be fractionated into a few hundred to a few thousand individual components. Many times this degree of resolution is sufficient, at which point antigens can be detected by fluorescence, absorbance, electrochemical, or some other means in which all analytes produce very similar characteristics for detection. These types of detection can be of very high sensitivity, yet still not discriminate between analytes. As such, analytes must be partially or totally resolved when they arrive at the detector.

Unlike traditional detection methods, mass spectrometry provides another, quite different detection method that is orthogonal in its mode of analysis. There are many types of mass spectrometers, several of which could be used in affinity selector based analyses of multiple analytes. The size exclusion methods described above examined the hydrodynamic volume of a substance. Multiple analytes may elute from a RAM or analytical RPC column together. Following ionization by either the MALDI or ESI process, analyte(s) are transported into a mass spectrometer where they are mass analyzed. Time-of-flight (TOF), quadrupole (Q), ion trap (IT), and hybrid forms of these instruments are used in mass analysis of analyte ions. As the name implies, mass spectrometry fractionates molecules on the basis of their mass, often to less than one atomic mass unit difference. Analytes thus analyzed (fractionated) are transported to an electron multiplier that produces an electrical signal, generally referred to as an ion current that can be used to quantify an analyte.

It can be the case that analyte ions of the same mass, or nearly the same mass, elute from the RAM, RPC, or some other type of chromatography column ahead of the MS elute together. This makes it impossible to differentiate between analytes that are up to this point in the analysis identical in their properties.

As a still higher dimension of analysis, it is possible to carry out some type of gas phase chemical reaction that causes ions from the first dimension to fragment. Collision induced dissociation (CID) and electron transfer dissociation (ETD) are two types of gas phase fragmentation strategies, but it should be understood and appreciated herein that there are others as well that can also be used in accordance with the present teachings. It is often the case in these gas phase reactions that molecules fragment in a manner unique to their structure. Fragment ions thus produced will also have unique masses that when analyzed in a second dimension of mass spectrometry can be recognized (by their mass) and quantified. Analyte quantification can be achieved from a single fragment ion or the sum of all fragment ions unique to an analyte.

Fragment ions from the second dimension of mass spectrometry can be selected and further fragmented in a third dimension of mass spectrometry to gain even more specificity, but the amount of ion involved relative to the origin is small and thus sensitivity is poor.

Mass spectrometers of choice in terms of sensitivity are those in which ions are produced and collected and/or analyzed continuously during the elution of a chromatographic peak and then further ionized and transported into the second dimension of MS for quantification. QQQ and IT-TOF instruments are examples. One of the great advantages of these instruments is that they collect many more ions for analysis.

Unfortunately, mass spectrometry based detection is not as sensitive as enzyme linked immunosorbent assay (ELISA) methods. For instance, current detection limits are in the range of 100 pg/mL, even when using 100 um internal diameter RPC columns before MS analysis. State-of-the-art ELISA, on the other hand, is 1000 times more sensitive. The enormous advantage of using mass spectrometry in the 4th, 5$^{th}$, and 6$^{th}$ dimensions of analysis, however, is specificity. Moreover, the MS analyses are very fast. In fact, tandem mass spectral analysis can generally be carried out in a second or less with most instruments. Still another advantage is that chromatographic retention time is integrated.

When analyte mixtures are simple and/or very high detection sensitivity is needed, going to high sensitivity liquid chromatography detectors is also possible in accordance with the teachings of the present invention. The advantage of using regular liquid chromatography (LC) detectors over the mass spectrometer is that they are far less expensive and can be of much higher sensitivity, especially when used with ~100 um ID capillaries. The sensitivity of an LC detector is inversely related to the square of column diameter. Going from the normal 4.6 mm ID column to a 100 um ID column of the same length increases detection sensitivity over 2000 fold. Using a 100 um ID RPC column and a laser induced fluorescence detector, the limit of detection with a 70 kD protein is approximately 1 pg/mL. This is in the range of ELISA, yet one is quantifying multiple antigens.

Still other detectors that may be used in accordance with the teachings of the present invention include, but are not limited to, laser induced fluorescence (LIF), electrochemical detection (EC), and absorbance detection (AB). Out of these detectors, the absorbance detector is by far the least sensitive. LIF and EC detection, on the other hand, generally requires that analytes be derivatized with a reagent that facilitates detection. In the case of LIF, this would be a fluorophore that exhibits excitation and emission wavelengths amenable to detection in the detector being used. The fluorescence tag agent must also react readily with analytes to facilitate the derivatization reaction.

It has been a practice for more than 50 years to add an internal standard to mixtures at known concentration and use the observed ratio of instrument response to the internal standard and analyte to determine analyte concentration. The great advantage of this approach is that it minimizes random errors that occur during sample analysis. With immunological assays, these measurements are generally referred to as competitive binding assays. The addition of an internal standard within an immunological assay is related to well-established RIA practices, where tagged synthetic molecules (Ag*) similar to antigens were added to samples. The function of the tag (*) was to enable detection, as the native antigen (Ag) in the sample could not be detected. When the two antigens $Ag_i$ and $Ag_i^*$ were added simultaneously and allowed to compete for a binding site from a limited amount of antibodies, this was referred to as a competitive binding assay and can be represented by the following illustrative equations:

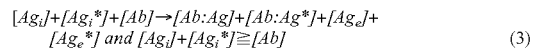

$$[Ag_i]+[Ag_i^*]+[Ab] \rightarrow [Ab:Ag]+[Ab:Ag^*]+[Ag_e]+ [Ag_e^*] \text{ and } [Ag_i]+[Ag_i^*] \geq [Ab] \quad (3)$$

where $[Ag_i]$ is the initial concentration of sample antigen, $[Ag_i^*]$ is the concentration of tagged antigen added to the sample initially in known concentration, $[Ag_e]$ is the final concentration of sample antigen after equilibration, and $[Ag_e^*]$ is the concentration of tagged antigen after final equilibration.

Here, the present invention is generally directed to differentiating between one hundred or more antigens (Ag) and tagged synthetic molecules (Ag*) simultaneously. This is enabled by liquid chromatography-mass spectrometry, which differentiates between all these species in a single analysis. As noted above, a particularly useful mode of running assays with large numbers of antigens is in the sequential addition, competitive binding assays with antibody saturation. The first step is to add a known amount of antibody $[Ab_1]$ (or antibodies with multiple antigens) to the sample that exceeds the amount of antigen $[Ag_i]$ in the sample. Such step can be represented by the following equation:

$$[Ag_i]+[Ab_1] \rightarrow [Ab_2:Ag]+[Ab_3] \quad (4)$$

where $[Ab_1]-[Ag_i] \approx [Ab_3]$. It is important to note above that $Ab_1$, $Ab_2$, and $Ab_3$ are the same antibody, however, at different points in the assay and under different conditions.

The second step of the assay is to add the tagged internal standard $[Ag_i^*]$ to the sample in known amount. The sum of the two antigens must exceed the concentration of the total amount of antibody targeting them, i.e. $[Ag_i]+[Ag_i^*][Ab]$ such that:

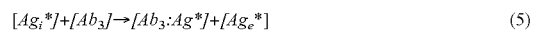

$$[Ag_i^*]+[Ab_3] \rightarrow [Ab_3:Ag^*]+[Ag_e^*] \quad (5)$$

Separation of $Ab_3:Ag^*$ from $Ag_e^*$ allows one to quantify $[Ab_3:Ag^*]$ alone. The concentration of $[Ab_3:Ag^*]$ in the sequential addition assay is inversely related to the concentration $[Ag_i]$, i.e. $Ab_3:Ag^*$ is at a maximum when $Ag_i$ approaches zero. Conversely, $Ab_3:Ag^*$ approaches zero as $Ag_i$ goes to large values. The sequential addition assay is linear as opposed to other forms of the competitive binding assay.

It is worth noting that the concentration of antigen being determined within the above-described assay controls, to a large extent, the amount of antibody and tagged antigen that must be added to carry out the assay. In other embodiments, such as the competitive binding Ab saturation assay described below, this is not the case. As such, it should be understood herein that the present teachings are not intended to be limited. A second notable point is that at the end of the reactions described in equations 3 and 5, both $Ab_2:Ag$ and $Ab_3:Ag^*$ coexist within the solution. Moreover, this is still true at the end of the separation step where $Ag_e^*$ is removed from the assay solution. The means that in terms of the detection of $Ab_3:Ag^*$, it is necessary that the tag allow discrimination between $Ab_2:Ag$ and $Ab_3:Ag^*$. Finally, it is also worth noting that differentiating between all the $Ab_3:Ag^*$ complexes from all the antigens is important to the above-described multiplexing processes, particularly as a different tag must be used for each antigen being determined. In the case of absorbance, fluorescence, and electrochemical based detection, however, this would probably amount to no more than the determination of five antigens.

In accordance with the competitive binding assays of the present invention, all the analytes should be structurally different to be detected for the multiplexed assays, including the internal standards added (e.g., isotopically coded internal standards to achieve relative or absolute quantification of the analytes) to the assay solution. As such, the assays will either have a different chromatographic retention time, a different molecular weight, or will fragment in a unique way in a mass spectrometer. In accordance with the above-described antigens, Ag* will either be a $^{13}C$, $^{14}N$, $^{18}O$, or $^2H$ labeled version of the antigen or carry some combination of these isotopes that give the internal standard antigen a uniquely different mass than the unlabeled, natural version of Ag. An alternative coding strategy will be to derivatize antigens with some moiety that does not alter their antigenicity but gives them mass spectral properties that are uniquely different than Ag and structurally different from any other substance in the solution. Labels in the case of derivatization will frequently be heavy isotope coded and may be a universal coding agent that in one isotopic form, is used to code all antigens (Ag) and in an isotopically different version, is used to globally code all internal standard antigens added to the solution, i.e. Ag* in equation 5. When the final assay mixture described in equation 5 is subjected to RPC-MS/MS analysis, it will be possible to discriminate between thousands of antigens in the same sample. Advantageously, the teachings of the present invention make it possible to identify and discriminate between thousands of antigens in a single analysis, thereby allowing thousands of immunological assays to be carried out simultaneously without immobilizing hundreds to thousands of antibodies or some other binding protein at specific array elements on a surface.

Focusing on Equation 3 above, the present teachings describe a case in which Ag and the internal standard antigen Ag* compete for a binding site on the antibody. Taking this general concept into consideration, the below described conditions also apply in accordance with certain assay embodiments of the present invention: $[Ag_i]+[Ag_i^*]>[Ab]$ for all antigens being assayed, and the concentration of $[Ag_i^*]$ added to the solution is within 5-fold of $[Ag_i]$. Moreover, the concentration of the internal standard $[Ag_i^*]$ added is known precisely, and the [Ab:Ag]/[Ab:Ag*] ratio is measured at the end of the assay. In accordance with this embodiment, large numbers of antigens are measured, i.e. $Ag_a, Ag_b, Ag_c, \ldots Ag_n$, and the antigens are capable of greatly varying in concentration, i.e. thousands of fold. In some embodiments, the same concentration is roughly used for all the antibodies, while in other embodiments, the concentration of antibody may be roughly and not precisely known. Finally, the ratios of Ag to Ag* will be determined in the manner described above, and is generally through differential isotope labeling or global internal standard labeling methods.

It should be understood and appreciated herein that in accordance with some teachings of the present invention, adding a known concentration of internal standard antigen makes it possible to determine the ratio of antigen to internal standard at the end of the assay. In accordance with these embodiments, it is possible to determine antigen concentration using the well known internal standard method. Moreover, when antibody concentration is matched to the optimum sensitivity range of the detection system, it is also possible to use the antibody as a sampling tool. In accordance with this sampling scheme, an amount of sample can be selected that matches the sensitivity of the detector without taking into consideration the antigen concentration, as well as can be used to bring antigens into a concentration range that varies no more than ten fold, regardless of their initial concentration. In accordance with these embodiments, antibody concentration is being used to bring analyte and internal standard concentration into the detection range of the measurement device used for quantification. Regardless of the optimum detection range of the monitoring system, it should be understood and appreciated herein that it is possible to bring analyte concentration into the optimal range of any detector, including a mass spectrometer. Ultimately, these described embodiments are capable of using antibody concentration to sample analytes and bring them all to a similar concentration range that matches the detection system, while the actual concentration is determined by the analyte to internal standard ratio.

Detection systems ranging from mass spectrometry through optical, electrochemical, interferometry, and surface plasmon resonance have been described above. Other than mass spectrometry, quantification processes in accordance with the detection methods of the present invention are generally known in the art and therefore will not be discussed in great detail herein. In terms of mass spectrometry, however, quantification can be achieved in multiple ways depending on the ionization method. While ion current arising from the detection of ions following mass analysis is widely used for detection in mass spectrometry, the ionization efficiency of such methods varies widely between analytes. In fact, ionization efficiency can even vary in some cases with concentration and other unknown matrix components in the sample. A more detailed discussion of quantification by mass spectrometry can be found in the following journal article, the disclosure of which is incorporated by reference herein in its entirety, "Primary amine coding as a path to comparative proteomics." Regnier, Fred E;. Julka, Samir. Proteomics (2006), 6(14), 3968-3979.

Fortunately, isotopomers of an analyte ionize in a nearly identical fashion when presented to a mass spectrometer together. This means that the relative ion current seen for the heavy and light forms of an analyte accurately reflect the relative difference in their concentration. When one of the isotopomers is an internal standard of the analyte added at known concentration, the absolute concentration of the analyte of unknown concentration can be calculated. This is true with both electrospray ionization (ESI) and matrix assisted laser desorption ionization (MALDI). It is important that all the isotopomers of an analyte ionize under identical conditions, particularly to avoid isotopomers separating in RPC. When they exactly coelute they are experiencing identical matrix inhibitors of ionization. Relative standard deviations will vary by 6-8% with this detection method.

In accordance with certain aspects of the present invention, mass spectrometers for isotopomer ratio quantification, which are capable of sitting on an ion for long periods of time (seconds) while eluting from the RPC column are particularly useful because they allow many more ions to accumulate than with instruments that rapid scan the mass range of ions emerging from the RPC and fail to accumulate large numbers of ions for detection. Non-limiting examples of such instruments include the triple quadrupole and quadrupole ion trap instruments.

Direct quantification by ion current measurements are also useful in accordance with the teachings of the present invention, and particularly wherein larger measurement errors in the range of about 20% to about 30% can be accepted.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A multi-dimensional method for simultaneously analyzing multiple protein analytes within a sample solution, the method comprising:

adding affinity selectors to a sample solution containing protein analytes to be measured, the affinity selectors having an affinity for one or more of the analytes within the sample solution, wherein the affinity selectors include at least one of an antibody and an antibody fragment;

allowing immune complexes to form between the affinity selectors and the protein analytes;

partially or totally resolving the formed immune complexes from non-analyte substances initially within the sample solution;

dissociating the resolved immune complexes to form polypeptide analytes from proteolysis of the protein analytes;

separating the polypeptide analytes derived from the immune complexes from one another by capturing the polypeptide analytes through a surface adsorption process;

transferring the captured polypeptide analytes to a detection means; and resolving the polypeptide analytes with the detection means according to their mass-to-charge ratios.

2. The method of claim 1, wherein the step of partially or totally resolving the formed immune complexes comprises at least one of separating the protein analytes or formed immune complexes according to their hydrodynamic volume, targeting a unique structural feature of the immune complexes by using capture antibodies, and targeting a biotinylated feature with immobilized avidin.

3. The method of claim 1, wherein the step of separating the polypeptide analytes comprises at least one of separating the polypeptide analytes according to their hydrodynamic volume, adsorbing and differentially eluting the polypeptide analytes from a hydrophobic surface, targeting a unique structural feature of the polypeptide analytes through capture antibodies of the polypeptide analytes or formed immune complexes, capturing biotinylated affinity selectors with immobilized avidin, adsorbing and differentially eluting the polypeptide analytes from a charged surface, adsorbing and differentially eluting the polypeptide analytes from an immobilized metal affinity chelator, and adsorbing and differentially eluting the polypeptide analytes from a boronic acid rich surface.

4. The method of claim 1, wherein the polypeptide analytes include at least one of a protein analyte fragment, a protein analyte derivative and a polypeptide analyte isotopomer.

5. The method of claim 1, wherein the step of resolving the formed immune complexes comprises targeting a unique structural feature of the affinity selectors with an immobilized antibody, the unique structural feature including at least one of a distinctive natural structural feature of the affinity selectors, a hapten that has been conjugated to the affinity selectors and an immunogen conjugated to the affinity selectors.

6. The method of claim 1, wherein polypeptide analytes are separated as gas phase ions according to their mass-to-charge ratio using a mass spectrometer followed by detection through collision with a detector surface.

7. The method of claim 1, further comprising using isotopically coded internal standards of polypeptide analytes to achieve their relative or absolute quantification.

8. The method of claim 1, further comprising using sequential addition, competitive binding assays to achieve relative or absolute quantification of the protein analytes.

9. The method of claim 1, further comprising using antibody concentration to collect an aliquot of a polypeptide analyte from the sample solution, the collected aliquot fitting an optimum detection range of a device used to resolve the polypeptide analytes.

10. The method of claim 1, wherein the affinity selectors are tagged with at least one of a biotin, a hapten, and an oligonucleotide.

11. The method of claim 10, wherein the affinity selectors comprise biotinylated affinity selectors.

12. The method of claim 1, wherein the affinity selectors are tagged with at least one of DNA, RNA, and PNA.

* * * * *